United States Patent
Yamamoto

(10) Patent No.: US 8,604,782 B2
(45) Date of Patent: Dec. 10, 2013

(54) EDDY CURRENT SENSOR

(75) Inventor: Takanari Yamamoto, Toyota (JP)

(73) Assignee: Toyota Jidosha Kabushiki Kaisha, Aichi-ken (JP)

(*) Notice: Subject to any disclaimer, the term of this patent is extended or adjusted under 35 U.S.C. 154(b) by 245 days.

(21) Appl. No.: 13/203,091

(22) PCT Filed: Feb. 23, 2010

(86) PCT No.: PCT/IB2010/000344
§ 371 (c)(1),
(2), (4) Date: Aug. 24, 2011

(87) PCT Pub. No.: WO2010/097677
PCT Pub. Date: Sep. 2, 2010

(65) Prior Publication Data
US 2011/0304328 A1    Dec. 15, 2011

(30) Foreign Application Priority Data
Feb. 24, 2009   (JP) ................... 2009-041463

(51) Int. Cl.
*G01N 27/90* (2006.01)
(52) U.S. Cl.
USPC .......................... 324/240; 324/242
(58) Field of Classification Search
USPC .................. 324/239–243
See application file for complete search history.

(56) References Cited

U.S. PATENT DOCUMENTS

| | | | |
|---|---|---|---|
| 3,241,058 A | 3/1966 | Quittner | |
| 4,808,924 A * | 2/1989 | Cecco et al. | 324/220 |
| 5,619,136 A * | 4/1997 | Drury | 324/242 |
| 6,952,095 B1 | 10/2005 | Goldfine et al. | |

FOREIGN PATENT DOCUMENTS

| | | |
|---|---|---|
| EP | 1 674 860 A2 | 6/2006 |
| JP | 63-298053 A | 12/1988 |
| JP | 2003-270214 A | 9/2003 |
| JP | 2006-046909 A | 2/2006 |
| JP | 2006-177949 A | 7/2006 |
| JP | 2006-226884 A | 8/2006 |
| JP | 2008-134106 A | 6/2008 |
| JP | 2009-545732 A | 12/2009 |

OTHER PUBLICATIONS

International Search Report and Written Opinion for corresponding International Patent Application No. PCT/IB2010/000344 mailed Jun. 17, 2010.
Japanese Office Action for corresponding JP Patent Application No. 2009-041463 drafted Jan. 27, 2011.

* cited by examiner

*Primary Examiner* — Jay Patidar
(74) *Attorney, Agent, or Firm* — Sughrue Mion, PLLC

(57) ABSTRACT

An eddy current sensor includes: an excitation coil that applies a predetermined alternating-current excitation signal to a measurement target component; and a detection coil that detects a detection signal, generated by eddy current, from the measurement target component to which the alternating-current excitation signal is applied. The excitation coil has a plurality of solenoid coils. The detection coil is arranged at least on one of two sides of the excitation coil in a direction of a central axis of each solenoid coil. Then, the plurality of solenoid coils are arranged in parallel with one another so that winding directions of the adjacent solenoid coils are opposite to each other.

13 Claims, 17 Drawing Sheets

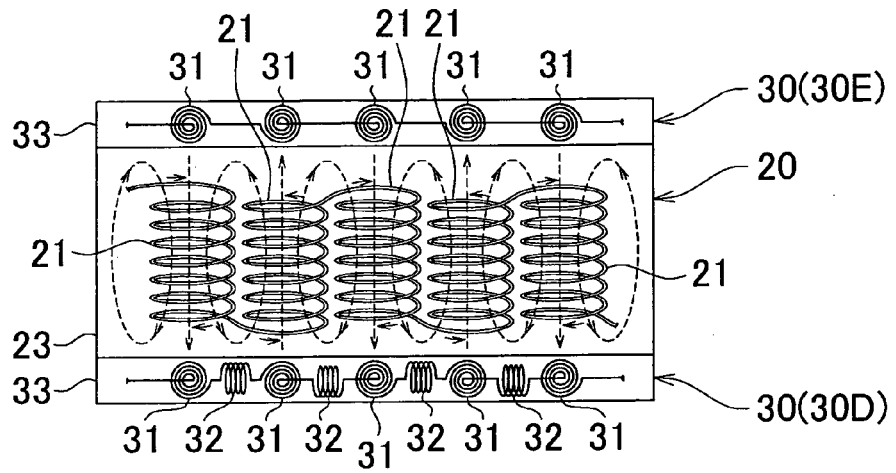
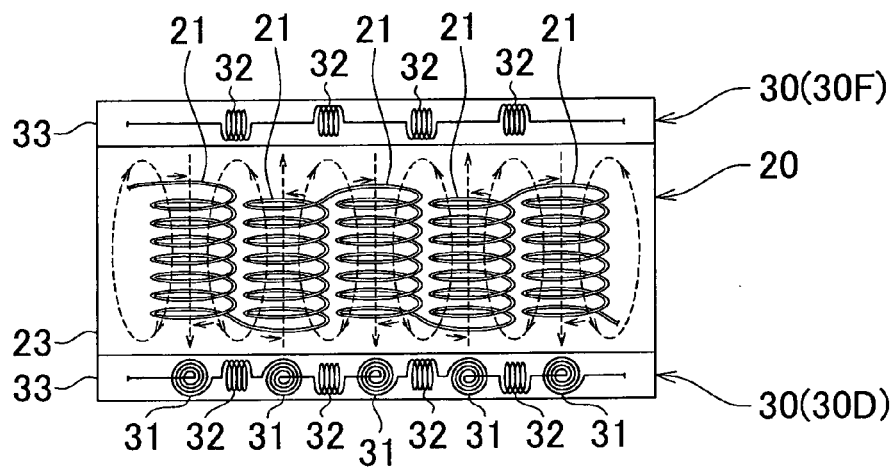
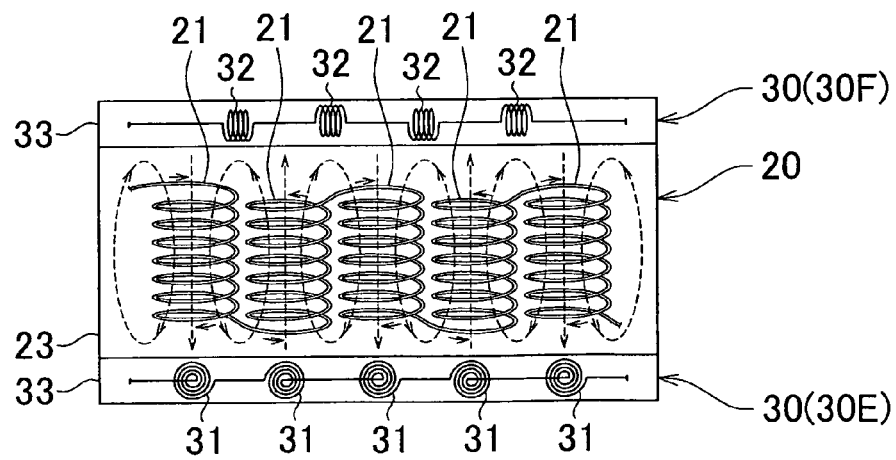

EDDY CURRENT SENSOR

BACKGROUND OF THE INVENTION

1. Field of the Invention

The invention relates to an eddy current sensor used for eddy current measurement that is performed in order to inspect the surface texture, cracks, and the like, of a steel product by utilizing eddy current, and also to an inspection method using the eddy current sensor.

2. Description of the Related Art

In an existing art, for the purpose of nondestructive inspection on the surface texture, cracks, and the like, of a quench-hardened layer, or the like, in a steel product, eddy current measurement has been conducted. The eddy current measurement is a measurement utilizing eddy current. The eddy current measurement is conducted using an excitation coil and a detection coil. The excitation coil is used to apply an alternating-current excitation signal to the steel product. The detection coil is used to detect a detection signal, generated by eddy current, from the steel product to which the alternating-current excitation signal is applied by the excitation coil. That is, in the eddy current measurement, a target steel product is magnetized by the excitation coil, and an induction magnetic field induced by the thus generated eddy current is detected by the detection coil. Thus, for eddy current measurement, the configuration that includes the excitation coil and the detection coil is used as a sensor (hereinafter, referred to as "eddy current sensor") included in a measurement system.

A technique related to eddy current measurement is, for example, described in Japanese Patent Application Publication No. 2008-134106 (JP-A-2008-134106). JP-A-2008-134106 describes a technique for inspecting a quenching pattern (quench-hardened layer) formed in a surface portion of a quenched component, such as an automobile component, by means of eddy current measurement. Specifically, in the technique described in JP-A-2008-134106, to determine whether the quenching pattern of a work piece (target steel product) is acceptable, a tolerance zone is set as a criterion in advance. Measured points of acceptable products are present in the tolerance zone within a plane in which a measured point determined by a value based on the phase difference of a detection signal from an alternating-current excitation signal and a value of the magnitude of the detection signal. Then, on the basis of whether a measured point regarding an inspection region of a work piece measured using the eddy current sensor falls within the tolerance zone, it is determined whether the quenching pattern of the work piece is acceptable.

Of course, with the technique described in JP-A-2008-134106, 100 percent inspection may be performed by means of in-line nondestructive inspection in terms of the quenching quality (quench depth, quenched hardness) of a component quenched by induction quenching, or the like. The quenching quality has been assured only through cutting inspection, or the like, by sampling. However, the eddy current measurement described in JP-A-2008-134106 has the following problem in terms of the structure of the eddy current sensor.

That is, as shown in FIG. 21A, in JP-A-2008-134106, a through-type coil 110 is used as an eddy current sensor. The through-type coil 110 is formed so that an excitation coil and a detection coil are accommodated in a case 111 made of synthetic resin, or the like, in a state where the excitation coil and the detection coil are arranged coaxially. The through-type coil 110 has a through hole 111a defined by the case 111. The through hole 111a is provided at a portion (inner peripheral portion) corresponding to a coil hollow portion of the excitation coil and detection coil that are accommodated in the case 111. That is, in the through-type coil 110, the excitation coil and the detection coil are provided so that the position of the common central axis substantially coincides with the position of the central axis of the through hole 111a.

The through-type coil 110 is used so that a shaft portion 112 of a work piece, which is a shaft-like (columnar) component, is inserted through the through hole 111a of the case 111. That is, with the through-type coil 110, in a state where the shaft portion 112 of the work piece is inserted through the through hole 111a, eddy current measurement for inspecting the quenching pattern is conducted on the shaft portion 112.

With the thus configured through-type coil 110, a sufficiently strong magnetic field tends to be obtained in eddy current measurement. In addition, with the through-type coil 110, because of the distribution of magnetic flux densities, there is a small influence of a variation in distance between the measurement portion of a work piece and the through-type coil 110 (distance in the radial direction (for example, the direction indicated by the arrow X1) of the coil) on a measured value, so it is possible to obtain a stable measured value.

However, in the eddy current measurement conducted using the through-type coil 110, a measurement target will be only a shaft portion of a shaft-like component, such as the shaft portion 112 of the work piece. That is, in the eddy current measurement conducted using the through-type coil 110, only the shaft portion of a shaft-like component, which may be inserted through the through hole 111a, can be a measurement target. Thus, the through-type coil 110, which serves as an eddy current sensor, cannot accept a portion, which cannot be inserted through the through hole 111a, as a measurement target. The portion that cannot be inserted through the through hole 111a, for example, includes a journal portion and pin portion of a crankshaft, and a curved portion formed between a shaft portion and proximal portion of an outer race that constitutes a bearing.

On the other hand, the eddy current sensor used in the existing art includes a probe-type coil 120 as shown in FIG. 21B. The probe-type coil 120 is formed so that a coil, such as a solenoid coil, is provided inside along a shaft-like (columnar) case 121, and has a detecting portion 122 at one end thereof. With the probe-type coil 120, the detecting portion 122 provided at one end of the columnar probe-type coil 120 is brought close to a measurement portion to conduct eddy current measurement. Thus, as shown in FIG. 21B, with the probe-type coil 120, a journal portion 123a or pin portion 123b of a crankshaft 123, which cannot be measured by the through-type coil 110 shown in FIG. 21A, may be set as a measurement target.

However, in the case of the probe-type coil 120, the strength of a magnetic field is lower than that of the through-type coil 110, so it is difficult to obtain a magnetic field having a strength sufficient for eddy current measurement. In addition, with the probe-type coil 120, because of the distribution of magnetic flux densities, there is a large influence of a variation in distance between the measurement portion of a work piece (crankshaft 123) and the probe-type coil 120 (distance in a direction (see the arrow X2) in which the detecting portion 122 is brought close to the work piece) on a measured value. Therefore, with the probe-type coil 120, a measured value is extremely sensitive to a variation in distance between the measurement portion and the probe-type coil 120, so it is difficult to obtain a reproducible and stable measured value. For these reasons, the probe-type coil 120 is currently not practical for inspecting the quenching quality.

Note that, in order to increase the strength of the magnetic field generated by the probe-type coil 120, it is conceivable that the number of turns of the coil is increased or an electric current that flows through the coil is increased. However, an increase in the strength of the magnetic field through these methods is limited because of a resistance in the coil.

As described above, in the foregoing description, practical eddy current measurement that enables 100 percent inspection by means of in-line nondestructive inspection is a measurement only on a shaft portion of a shaft-like component using the through-type coil. That is, currently, it is desired to implement an eddy current sensor that allows eddy current measurement on a component having a relatively complex shape, such as a journal portion or pin portion of a crankshaft (other than a shaft portion of a shaft-like component).

SUMMARY OF THE INVENTION

The invention provides an eddy current sensor and an inspection method using the eddy current sensor, which allow a portion having a shape, other than a shaft portion of a shaft-like component, to be set as a measurement target and are able to extend the range of application of eddy current measurement.

An aspect of the invention provides an eddy current sensor. The eddy current sensor includes: an excitation coil that applies a predetermined alternating-current excitation signal to a measurement target component; and a detection coil that detects a detection signal, generated by eddy current, from the measurement target component to which the alternating-current excitation signal is applied. The excitation coil has a plurality of solenoid coils. The detection coil is arranged at least on one of two sides of the excitation coil in a direction of a central axis of each solenoid coil. Then, the plurality of solenoid coils are arranged in parallel with one another so that winding directions of the adjacent solenoid coils are opposite to each other.

With the eddy current sensor according to the above aspect, it is possible to set a portion having a shape, other than a shaft portion of a shaft-like component, as a measurement target, and it is possible to extend the range of application of eddy current measurement.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein:

FIG. 11A is a view that shows a fifth alternative configuration of the eddy current sensor according to the first embodiment of the invention;

FIG. 11B is a view that shows a sixth alternative configuration of the eddy current sensor according to the first embodiment of the invention;

FIG. 11C is a view that shows a seventh alternative configuration of the eddy current sensor according to the first embodiment of the invention;

DETAILED DESCRIPTION OF EMBODIMENTS

The invention is directed to extending the range of application of eddy current measurement in such a manner that an excitation coil and detection coil of an eddy current sensor used for eddy current measurement (hereinafter, referred to as "eddy current sensor") each are formed of a plurality of coils and the arrangement of those coils, a method of coupling those coils, and the like, are devised. Hereinafter, embodiments of the invention will be described. Note that the embodiments of the invention mainly describe a case where eddy current measurement is conducted using an eddy current sensor for inspecting the quenching quality (quench depth, quenched hardness) of a component quenched by induction quenching, or the like. That is, in terms of the quenching quality, the eddy current sensor is used to conduct eddy current measurement to thereby inspect a quenched component, which is a measurement target component.

Figure 1:
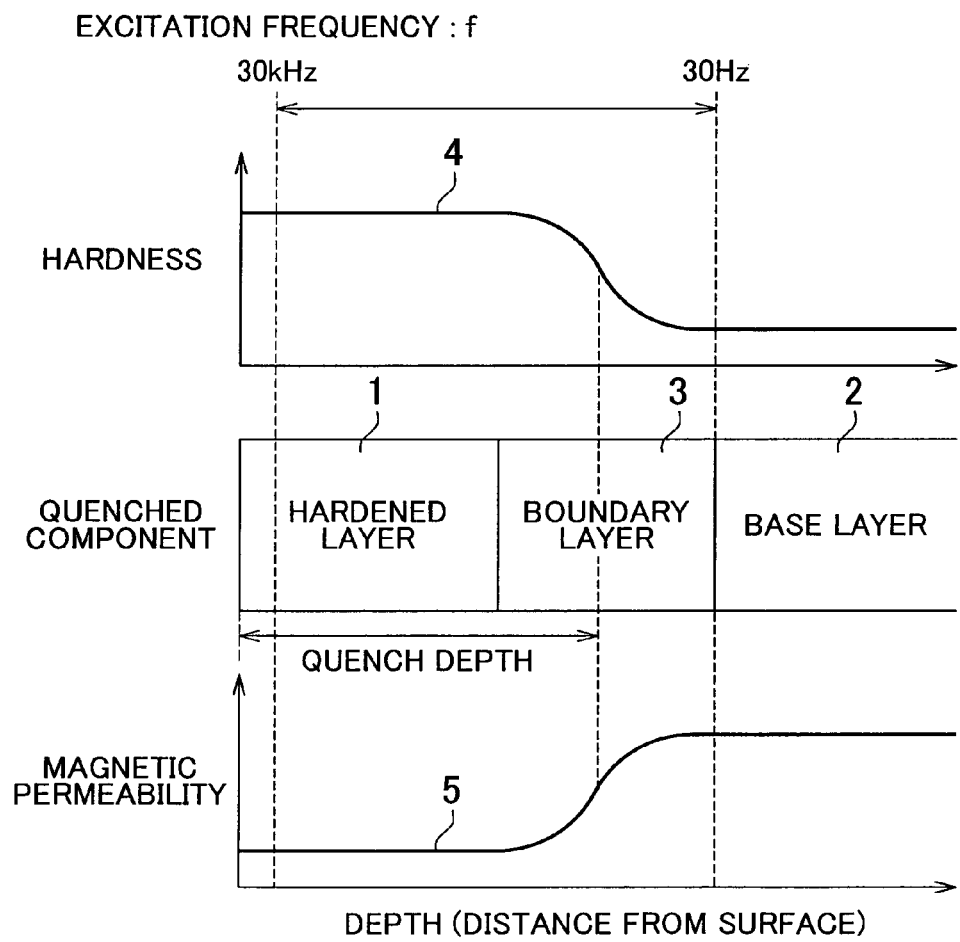
FIG. 1 is a graph that shows the relationship among the state of a layer, hardness and magnetic permeability of a quenched component in the depth direction.

FIG. 1 is a graph that shows the relationship among the state of a layer, hardness and magnetic permeability of the quenched component, which is a steel product (S45C, or the like) subjected to quenching, in the direction of depth (distance from the surface). As shown in FIG. 1, in the quenched component, a hardened layer 1 and a base layer 2 are formed in order from the surface side via a boundary layer 3 as the schematic texture configuration of the quenched component. The hardened layer 1 is a portion subjected to quenching. The base layer 2 is a base material portion. By referring to a hardness change curve 4, the hardened layer 1 and the base layer 2 have different hardnesses, and the hardness of the hardened layer 1 is higher than that of the base layer 2. In the boundary layer 3, the hardness gradually reduces from a side adjacent to the hardened layer 1 toward the base layer 2. A specific example of the hardness in Vickers hardness (Hv) is such that the hardened layer 1 has a hardness of 600 to 700 Hv, and the base layer 2 has a hardness of about 300 Hv.

On the other hand, by referring to a magnetic permeability change curve 5, a variation in magnetic permeability against a distance from the surface of the quenched component is substantially inversely proportional to a variation in hardness against a distance from the surface of the quenched component. That is, the magnetic permeability of the hardened layer 1 is higher than that of the base layer 2, and gradually increases in the boundary layer 3 from a side adjacent to the hardened layer 1 toward the base layer 2. In the eddy current measurement according to the present embodiment, the relationship between a hardness and a magnetic permeability against a distance from the surface of the quenched component is utilized.

Figure 2:
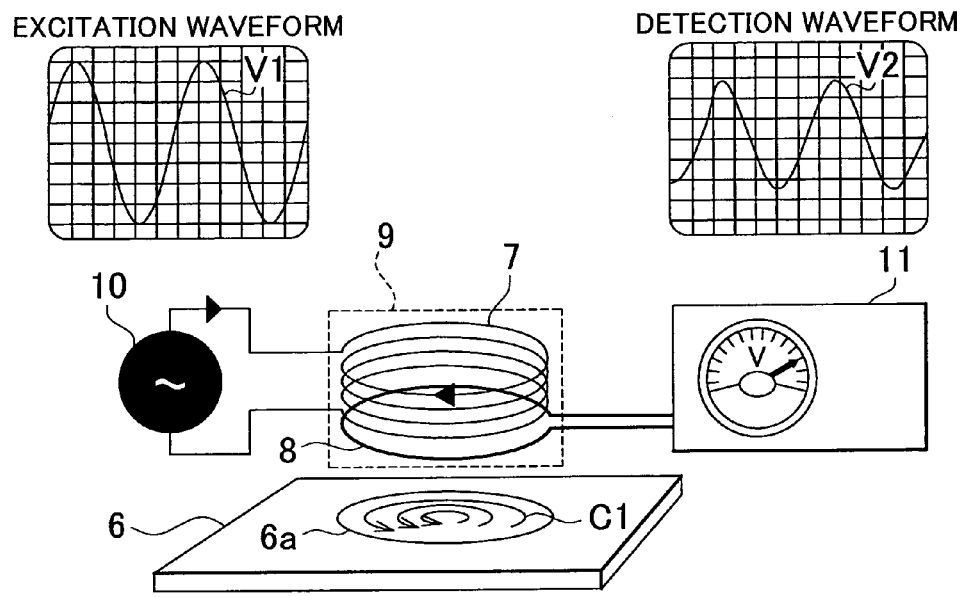
FIG. 2 is a schematic view that shows the system configuration for conducting eddy current measurement according to an embodiment.

The schematic system configuration (principle of measurement) for conducting eddy current measurement according to the present embodiment will be described with reference to FIG. 2. As shown in FIG. 2, in the eddy current measurement, an eddy current sensor 9 having an excitation coil 7 and a detection coil 8 is set at a predetermined position with respect to a measurement portion 6a of a work piece (magnetic material) 6, which is a measurement target component. In the above configuration, as the excitation coil 7 is supplied with electric current, a magnetic field appears around the excitation coil 7. Then, eddy current is generated in proximity to the surface of the measurement portion 6a of the work piece 6, which is the magnetic material, through electromagnetic induction (see the arrow C1). As eddy current is generated on the surface of the measurement portion 6a, a magnetic flux penetrates through the detection coil 8. Then, an induced voltage attended with generation of eddy current on the surface of the measurement portion 6a is measured by the detection coil 8.

Both ends (both terminals) of the excitation coil 7 are connected to an alternating-current power supply 10. The alternating-current power supply 10 applies a predetermined alternating-current excitation signal (excitation alternating-current voltage signal) V1 to the excitation coil 7. Both ends (both terminals) of the detection coil 8 are connected to a measurement device 11. The measurement device 11 detects the magnitude of a detection signal (a voltage signal regarding the induced voltage) V2 obtained from the detection coil 8 when the alternating-current excitation signal V1 is applied from the alternating-current power supply 10 to the excitation coil 7 and a phase difference (phase delay) Φ (see FIG. 3) of the detection signal V2 with respect to the alternating-current excitation signal V1. Here, in order to detect the phase difference Φ, the measurement device 11 is supplied with the alternating-current excitation signal V1 (waveform) as an amplified phase detection signal.

Figure 3:
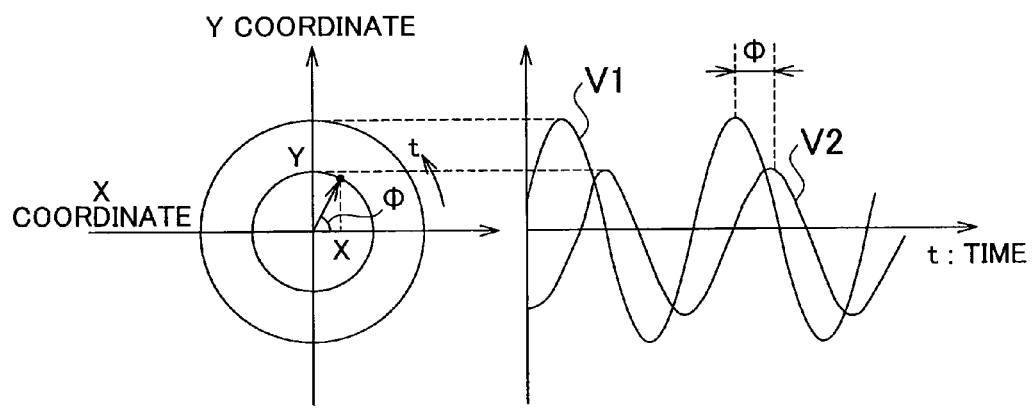
FIG. 3 is a graph that shows the relationship between an alternating-current excitation signal and a detection signal in eddy current measurement.

The detection signal V2 detected by the detection coil 8 reflects the magnetic permeability of the measurement portion 6a (work piece 6). That is, as the magnetic permeability of the measurement portion 6a increases, a magnetic flux attended with generation of eddy current as described above increases, so the magnitude of the detection signal V2 increases. Conversely, as the magnetic permeability of the measurement portion 6a decreases, a magnetic flux attended with generation of eddy current reduces, so the magnitude of the detection signal V2 decreases. In order to quantify (digitize) the detection signal V2 based on the eddy current, as shown in FIG. 3, an amplitude value Y that is a value of the magnitude of the detection signal V2 and a value X (=Y cos Φ) that is a value based on the phase difference Φ of the detection signal V2 with respect to the alternating-current excitation signal V1 are focused, and the following findings are known.

First, the amplitude value Y of the detection signal V2 may correlate with the quenched surface hardness (hardness of a quenched portion). That is, as is apparent from a comparison between the hardness change curve 4 and the magnetic permeability change curve 5 shown in FIG. 1, there is a relationship that the magnetic permeability increases as the quenched surface hardness decreases. As the magnetic permeability increases, a magnetic flux generated when the alternating-current excitation signal V1 is applied to the excitation coil 7 increases, so eddy current induced on the surface of the measurement portion 6a also increases. In accordance with this, the amplitude value Y of the detection signal V2 detected by the detection coil 8 also increases. Thus, conversely, a magnetic flux that penetrates through the measurement portion 6a at which eddy current is generated, that is, a magnetic permeability, is derived from the amplitude value Y of the detection signal V2 detected by the detection coil 8. By so doing, the quenched surface hardness is obtained from the relationship between the hardness change curve 4 and the magnetic permeability change curve 5 that are shown in FIG. 1.

Next, the value X based on the phase difference Φ of the detection signal V2 with respect to the alternating-current excitation signal V1 may correlate with the quench depth (the depth of a hardened layer). That is, an increase in the quench depth, that is, an increase in the hardened layer 1 quenched in the quenched component, means an increase in the low magnetic permeability range in the depth direction, so the phase delay of the detection signal V2 with respect to the alternating-current excitation signal V1 increases. Thus, the degree of the quench depth is obtained from the magnitude of the value based on the phase difference Φ.

In the eddy current measurement for inspecting the quenching quality of a quenched component on the basis of the above principle of measurement, the eddy current sensor having the excitation coil and the detection coil are used as described above. Hereinafter, the configuration of the eddy current sensor will be described as the embodiments of the invention.

Figure 4:
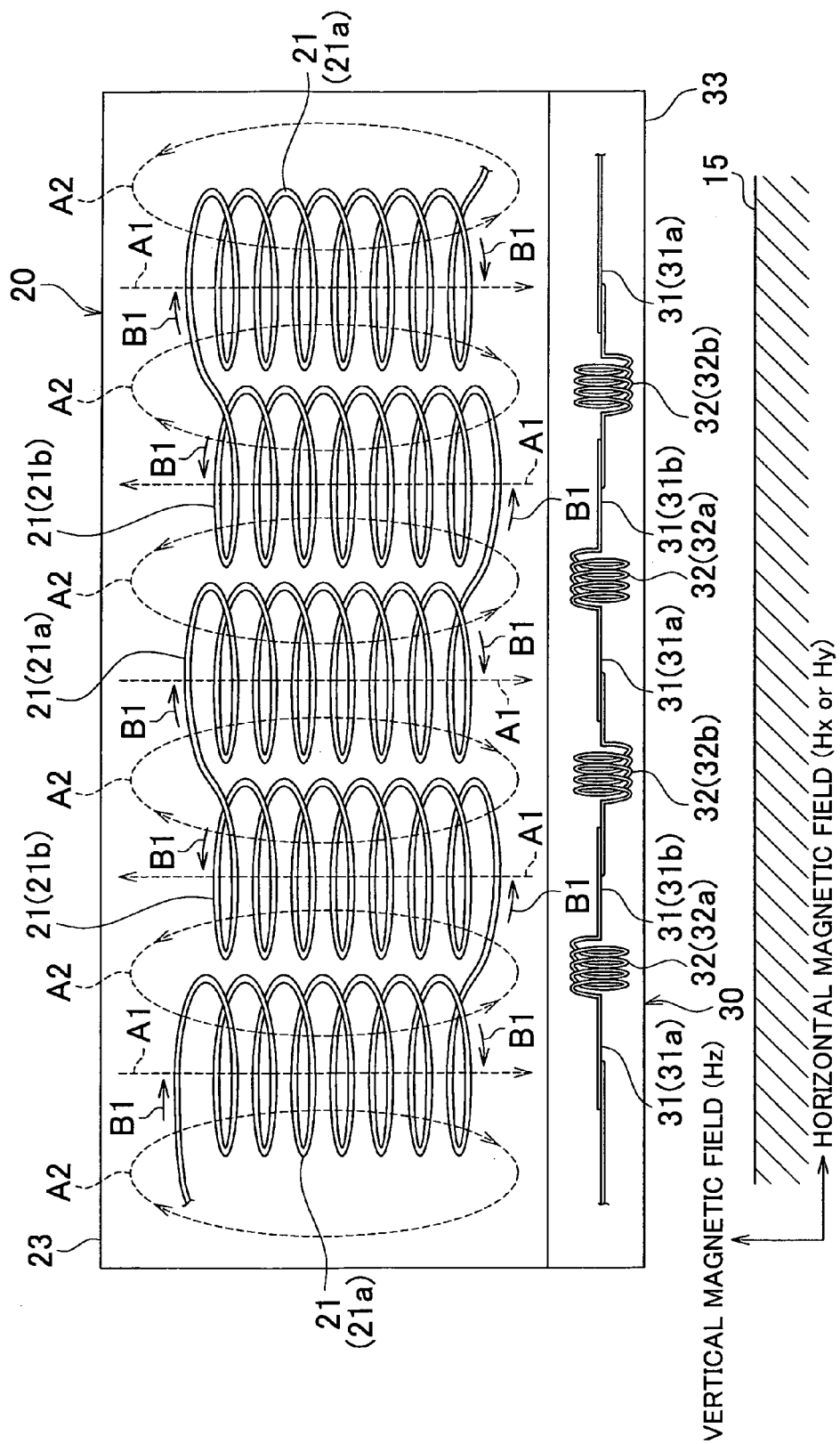
FIG. 4 is a view that shows the configuration of an eddy current sensor according to a first embodiment of the invention.
Figure 5:
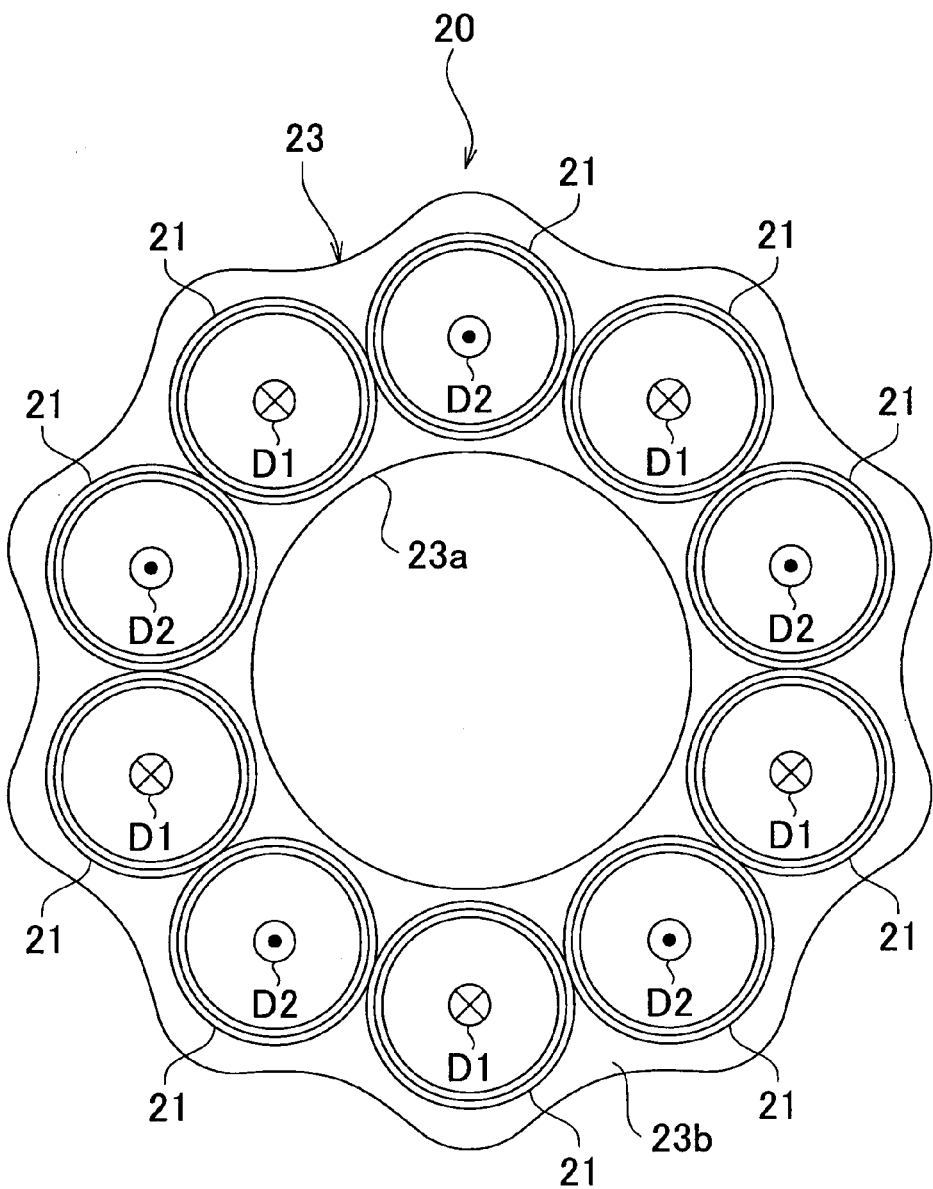
FIG. 5 is a view that shows the configuration of an excitation coil according to the first embodiment of the invention.
Figure 6:
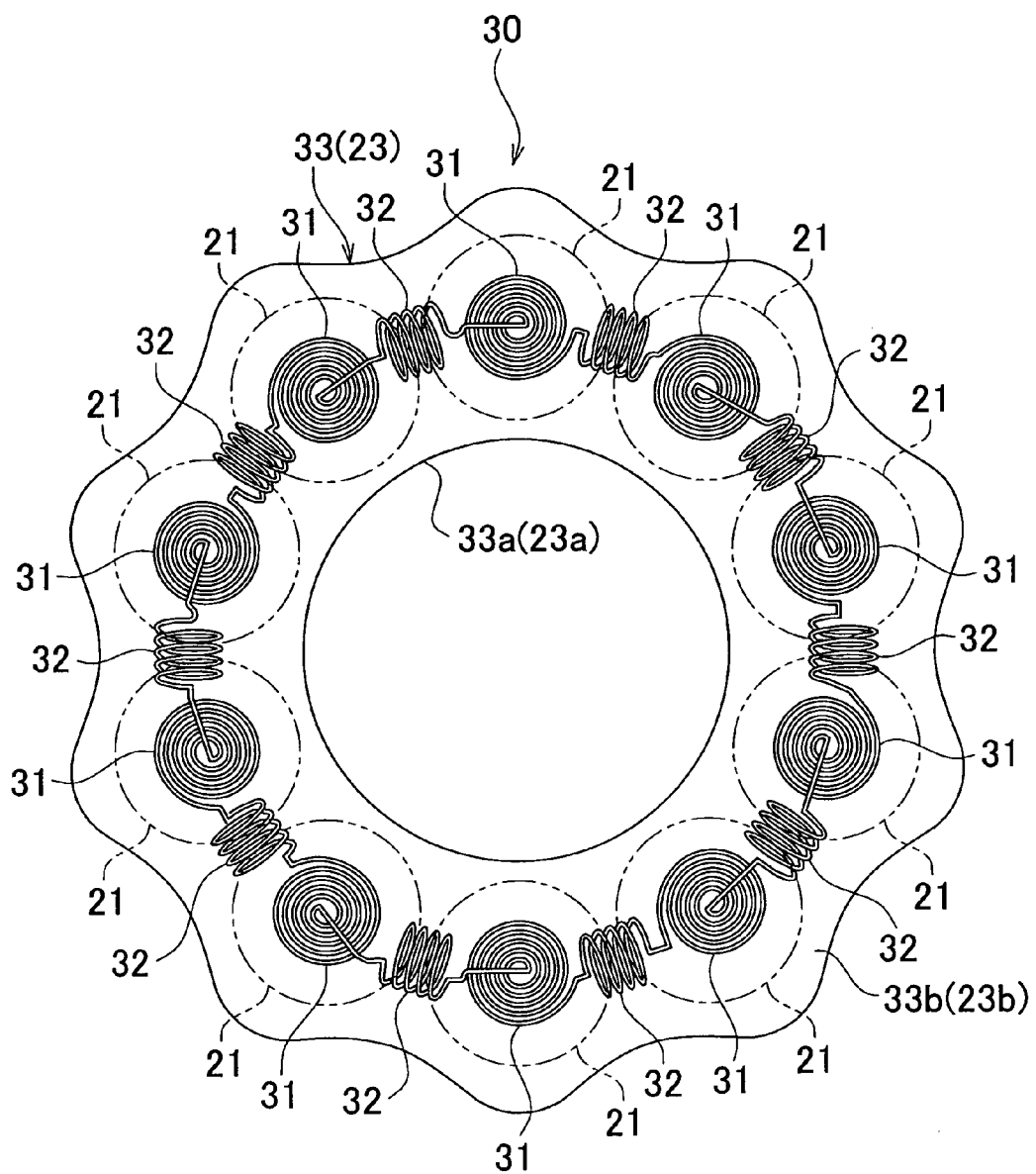
FIG. 6 is a view that shows the configuration of a detection coil according to the first embodiment of the invention.

A first embodiment of the invention will be described. As shown in FIG. 4 to FIG. 6, an eddy current sensor according to the present embodiment has an excitation coil 20 and a detection coil 30. The excitation coil 20 is used to apply a predetermined alternating-current excitation signal (see the above alternating-current excitation signal V1) to a work piece 15. The detection coil 30 is used to detect a detection signal (see the above detection signal V2), generated by eddy current, from the work piece 15 to which the alternating-current excitation signal is applied.

Then, as shown in FIG. 4 and FIG. 5, the eddy current sensor according to the present embodiment includes a plurality of solenoid coils 21 as the excitation coil 20. Specifically, the eddy current sensor according to the present embodiment has the ten solenoid coils 21 (see FIG. 5). Each of the ten solenoid coils 21 has substantially the same length, diameter, number of turns, and the like.

The plurality of (ten) solenoid coils 21, which serve as the excitation coil 20, are arranged in parallel with one another. That is, the plurality of solenoid coils 21 are arranged side by side so that the central axes (cylinder axis directions of cylindrical shapes, hereinafter, referred to as "coil central axes") are substantially parallel to one another. Note that, in the following description, the vertical direction, which is a direction corresponding to the coil central axis direction in FIG. 4, is defined as the vertical direction of the eddy current sensor.

In addition, the plurality of solenoid coils 21 are configured so that the winding directions are alternate. Here, the phrase that "the winding directions are alternate" means that the directions (rotating directions) in which electric current flows along the solenoid coils 21 are opposite between the adjacent solenoid coils 21. That is, in the adjacent solenoid coils 21, the directions of magnetic fields generated inside the respective solenoid coils 21 (see the arrows A1 in FIG. 4, hereinafter, referred to as "vertical magnetic fields") in accordance with the corkscrew rule are opposite to each other.

The plurality of solenoid coils 21 are arranged in parallel with one another so that the winding directions are alternate, and the adjacent solenoid coils 21 are coupled to each other. In the present embodiment, as shown in FIG. 4, the plurality of coupled solenoid coils 21 are formed in such a manner that a single continuous lead wire is wound so that the upper or lower ends of the adjacent solenoid coils 21 are alternately coupled to each other.

Thus, as shown in FIG. 4, in the excitation coil 20, solenoid coils 21a and solenoid coils 21b are alternately present as the solenoid coils 21. In each solenoid coil 21a, the vertical magnetic field is generated in a downward direction when electric current flows in a predetermined direction (see the arrow B1). In each solenoid coil 21b, the vertical magnetic field is generated in an upward direction when electric current flows in the predetermined direction.

Here, in FIG. 5, a marked portion indicated by the reference sign D1 or the reference sign D2 in each solenoid coil 21 indicates the direction of the vertical magnetic field in each solenoid coil 21. The reference sign D1 indicates that the vertical magnetic field is directed toward the far side in the vertical direction with respect to the sheet of FIG. 5. The reference sign D2 indicates that the vertical magnetic field is directed toward the near side in the vertical direction with respect to the sheet of FIG. 5. As indicated by these reference signs D1 and D2, the directions of the vertical magnetic fields are alternate (opposite) between the adjacent solenoid coils 21.

In addition, in the excitation coil 20, electric current flows to cause interaction between the adjacent solenoid coils 21 to thereby generate revolving magnetic fields (see the arrows A2 in FIG. 4). That is, the revolving magnetic fields are generated in such a manner that parts of the vertical magnetic fields generated in the respective adjacent solenoid coils 21 reinforce each other. Each revolving magnetic field is an annular magnetic field that penetrates through the adjacent solenoid coils 21 and that extend along the direction to revolve through the insides of both adjacent coils.

As described above, in the excitation coil 20, the magnetic fields generated by the flow of electric current include the vertical magnetic fields (see the arrows A1) generated inside the respective solenoid coils 21 and the revolving magnetic fields (see the arrows A2) generated by the interaction between the adjacent solenoid coils 21. The vertical magnetic fields and revolving magnetic fields are generated in the excitation coil 20 in this way, and are applied to the work piece 15 to generate eddy current. Then, the generated eddy current is detected by the detection coil 30.

In the eddy current sensor according to the present embodiment, the detection coil 30 is arranged on one side (lower side) of the excitation coil 20 in the coil central axis direction. The detection coil 30 is sensitive to at least any one of the vertical magnetic fields and revolving magnetic fields generated in the excitation coil 20.

When the detection coil 30 is sensitive to the vertical magnetic fields, the detection coil 30 is sensitive in the coil central axis direction (vertical direction), which is the direction of the vertical magnetic fields on one side of the excitation coil 20 in the coil central axis direction. In addition, when the detection coil 30 is sensitive to the revolving magnetic fields, the detection coil 30 is sensitive in the direction of the revolving magnetic fields on one side of the excitation coil 20 in the coil central axis direction.

Here, the direction of the revolving magnetic fields on one side of the excitation coil 20 in the coil central axis direction is parallel to a plane perpendicular to the coil central axis (horizontal direction with respect to the vertical direction). That is, when the direction of the vertical magnetic fields is a z direction, the direction of the revolving magnetic fields on one side of the excitation coil 20 in the coil central axis direction is parallel to an x-y plane.

Thus, the detection coil 30 is sensitive to at least any one of a vertical magnetic field (Hz) that is a magnetic field in the vertical direction and a horizontal magnetic field (Hx or Hy) of a revolving magnetic field. That is, the detection coil 30 detects a variation in a vertical magnetic field (Hz) when the detection coil 30 is sensitive to a vertical magnetic field (Hz), and detects a variation in a horizontal magnetic field (Hx or Hy) when the detection coil 30 is sensitive to a horizontal magnetic field (Hx or Hy).

The vertical magnetic fields (Hz) and horizontal magnetic fields (Hx or Hy) that are generated in the excitation coil 20 respectively have the following characteristics in eddy current measurement. The vertical magnetic fields (Hz) have an advantage such that the strengths of the magnetic fields are relatively high and sufficiently strong magnetic fields may be easily obtained in eddy current measurement. Conversely, the vertical magnetic fields (Hz) have a characteristic such that, because of the distribution of magnetic flux densities, there is a relatively large influence of a variation in distance between a measurement portion of the work piece 15 and the excitation coil 20. Therefore, a measured value in eddy current measurement is sensitive to a variation in distance between the work piece 15 and the excitation coil 20.

On the other hand, the horizontal magnetic fields (Hx or Hy) have an advantage such that, because of the distribution of magnetic flux densities, there is a relatively small influence of a variation in distance between the measurement portion of the work piece 15 and the excitation coil 20. Therefore, a measured value in eddy current measurement is rarely influenced by a variation in distance between the work piece 15 and the excitation coil 20. Conversely, the horizontal magnetic fields (Hx or Hy) have a characteristic such that the strengths of the magnetic fields are relatively low and it is difficult to obtain sufficiently strong magnetic fields in eddy current measurement.

In addition, in the eddy current sensor according to the present embodiment, the plurality of solenoid coils 21 that constitute the excitation coil 20 are annularly arranged. That is, as shown in FIG. 5, in the eddy current sensor according to the present embodiment, the ten solenoid coils 21 of the excitation coil 20 are arranged annularly in position such that the coil central axes of them are substantially parallel to one another.

In the eddy current sensor according to the present embodiment, the plurality of solenoid coils 21 that constitute the excitation coil 20 are supported by a first housing 23 in the above described arrangement and coupled state. In the present embodiment, the first housing 23 is formed of a resin member having a predetermined shape.

Then, in the excitation coil 20, the first housing 23 is formed so that the plurality of solenoid coils 21 are buried by resin. That is, for example, resin is poured into a die that has a predetermined shape and in which the plurality of solenoid coils 21 are set in the above described arrangement and coupled state, and then the resin is cured, thus forming the first housing 23. Therefore, the plurality of solenoid coils 21 are buried in the resin first housing 23.

In the case of the present embodiment, the plurality of solenoid coils 21 are supported in a state where they are buried in the first housing 23. This prevents oxidation of the solenoid coils 21 due to contact with air, so it is desirable in terms of durability of the excitation coil 20. Alternatively, the first housing 23 may be formed as a hollow case member having a space for accommodating the plurality of solenoid coils 21. In this case, the plurality of solenoid coils 21 are accommodated in the space inside the first housing 23, and are supported in the above described arrangement and coupled state. In addition, the material that constitutes the first housing 23 is also not specifically limited as long as the material does not influence the magnetic fields generated by the solenoid coils 21 (or the material has a negligible influence on the magnetic fields).

As shown in FIG. 5, the first housing 23 has a through hole 23a at a portion surrounded by the plurality of solenoid coils 21 that are annularly arranged. The through hole 23a is formed by a cylindrical inner peripheral surface. The through hole 23a allows part of the work piece 15, which will be measured by the eddy current sensor according to the present embodiment, to be inserted therethrough.

In addition, the outer peripheral portion 23b of the first housing 23 has a wavy shape that is formed along the outer shapes of the solenoid coils 21 arranged annularly. That is, when viewed in the coil central axis direction as shown in FIG. 5, the outer peripheral portion 23b of the first housing 23 has a regularly concavo-convex shape such that, in the circumferential direction (a direction along the annular shape in which the plurality of solenoid coils 21 are arranged; the same applies to the following description), portions corresponding to the solenoid coils 21 are protrusions and portions between the adjacent solenoid coils 21 are recesses. In this way, the first housing 23 has a revolver shape of which the rotating direction is the circumferential direction.

As shown in FIG. 4 and FIG. 6, the eddy current sensor according to the present embodiment has pancake coils 31 and horizontal solenoid coils 32 as the detection coil 30. Each of the pancake coils 31 is formed so that a lead wire is circularly wound in a substantially single layer. Each pancake coil 31 is sensitive to a vertical magnetic field (Hz) formed by the excitation coil 20. That is, in the eddy current sensor according to the present embodiment, each pancake coil 31 functions as a first coil that is sensitive to a magnetic field (vertical magnetic field (Hz)) in the coil central axis direction.

Each horizontal solenoid coil 32 is a solenoid coil of which the central axis is aligned in the horizontal direction. Each horizontal solenoid coil 32 is sensitive to a horizontal magnetic field (Hx or Hy) formed by the excitation coil 20. That is, each horizontal solenoid coil 32 functions as a second coil that is sensitive to a magnetic field (horizontal magnetic field (Hx or Hy)) that is formed between the adjacent solenoid coils 21 and of which the direction is substantially perpendicular to the coil central axis of each solenoid coil 21.

The pancake coils 31 and the horizontal solenoid coils 32 that constitute the detection coil 30 are respectively arranged as follows with respect to the excitation coil 20. That is, each pancake coil 31 is arranged so that the position of the central axis substantially coincides with the position of the central axis of a corresponding one of the solenoid coils 21. That is, each disc-shaped pancake coil 31 is arranged coaxially with the solenoid coil 21 on one side (lower side), in the coil central axis direction, of each solenoid coil 21 that constitutes the excitation coil 20. In this way, each pancake coil 31 is arranged so as to be sensitive to a vertical magnetic field (Hz).

The horizontal solenoid coils 32 are arranged so that the central axis direction set in the horizontal direction substantially coincides with a direction in which the adjacent solenoid coils 21 are adjacent to each other (arrangement direction). That is, each horizontal solenoid coil 32 is arranged in position such that the central axis is aligned in the direction of the horizontal magnetic field (Hx or Hy) along the revolving magnetic field formed between the adjacent solenoid coils 21. Thus, in the eddy current sensor according to the present embodiment in which the plurality of solenoid coils 21 are arranged annularly, the horizontal solenoid coils 32 are arranged so that the central axes are oriented in substantially tangential directions of a circumferential shape that is aligned along the annular shape. The annular shape is the arrangement shape of the plurality of solenoid coils 21. In this way, the horizontal solenoid coils 32 are arranged so as to be sensitive to a horizontal magnetic field (Hx or Hy).

The pancake coils 31 and the horizontal solenoid coils 32 are arranged with respect to the excitation coil 20 (solenoid coils 21) in this way, and are alternately arranged in the direction in which the plurality of solenoid coils 21 are arranged. In the eddy current sensor according to the present embodiment in which the ten solenoid coils 21 are arranged annularly, ten pancake coils 31 and ten horizontal solenoid coils 32 are alternately arranged annularly along the arrangement of the solenoid coils 21.

Then, when focusing only on the pancake coils 31, the ten pancake coils 31 are formed so that the winding directions are alternate. That is, as shown in FIG. 4, in the detection coil 30, a pancake coil 31a for a downward vertical magnetic field (Hz) and a pancake coil 31b for an upward vertical magnetic field (Hz) are alternately present as the pancake coils 31.

Similarly, when focusing only on the horizontal solenoid coils 32, the ten horizontal solenoid coils 32 are formed so that the winding directions are alternate. That is, as shown in FIG. 4, in the detection coil 30, a horizontal solenoid coil 32a for a horizontal magnetic field (Hx or Hy) of one orientation (rightward in FIG. 4) in the direction in which the adjacent solenoid coils 21 are arranged side by side and a horizontal solenoid coil 32b for a horizontal magnetic field (Hx or Hy) of the other orientation (leftward in FIG. 4) in the direction in which the adjacent solenoid coils 21 are arranged side by side are alternately present as the horizontal solenoid coils 32.

In this way, the pancake coils 31 and the horizontal solenoid coils 32 are arranged so that the winding directions are alternate, and the adjacent coils are coupled to each other. In the present embodiment, as shown in FIG. 4 and FIG. 6, a single continuous lead wire is wound so that the pancake coils 31 and the horizontal solenoid coils 32 are alternately arranged and the adjacent coils are coupled to each other. By so doing, the plurality of alternately coupled pancake coils 31 and horizontal solenoid coils 32 are formed.

In addition, in the eddy current sensor according to the present embodiment, the plurality of pancake coils 31 and horizontal solenoid coils 32 that constitute the detection coil 30 are supported by a second housing 33 in the above described arrangement and coupled state. The second housing 33 is formed of a resin member having a predetermined shape as in the case of the first housing 23 of the excitation coil 20. That is, the plurality of pancake coils 31 and horizontal solenoid coils 32 are buried in the resin second housing 33. Note that as in the case of the first housing 23 of the excitation coil 20, the second housing 33 may be formed of a hollow case member, and the material that constitutes the second housing 33 is not specifically limited.

In addition, as shown in FIG. 6, the second housing 33 has a through hole 33a at a portion surrounded by the plurality of pancake coils 31 and horizontal solenoid coils 32 that are annularly arranged in correspondence with the plurality of solenoid coils 21. The through hole 33a is continuous with the through hole 23a of the first housing 23 of the excitation coil 20. That is, the through hole 33a in cooperation with the through hole 23a of the excitation coil 20 allows part of the work piece 15, which will be measured by the eddy current sensor according to the present embodiment, to be inserted therethrough. In addition, as in the case of the first housing 23 of the excitation coil 20, the outer peripheral portion 33b of the second housing 33 has a wavy shape that is formed along the outer shapes of the solenoid coils 21 arranged annularly.

The second housing 33 of the detection coil 30 is integrally formed with the first housing 23 of the excitation coil 20. Both housings 23 and 33 may be formed separately or may be formed integrally.

When the first housing 23 of the excitation coil 20 and the second housing 33 of the detection coil 30 are formed integrally, for example, an integral housing 23 shared by the excitation coil 20 and the detection coil 30 are formed as follows. That is, resin is poured into a die that has a predetermined shape and in which the plurality of solenoid coils 21, the pancake coils 31 and the horizontal solenoid coils 32 are set in the above described arrangement and coupled state, and then cured. Thus, the integral housing 23 is formed. In this case, the plurality of solenoid coil 21, the pancake coils 31 and the horizontal solenoid coils 32 are buried in the integral housing having the through hole 23a and the outer peripheral portion 23b.

The thus configured eddy current sensor is used to conduct eddy current measurement for inspecting the quenching quality of the work piece 15. The inspection method using the eddy current sensor is as follows. That is, to conduct eddy current measurement, the eddy current sensor is brought close to the measurement portion of the work piece 15 from the detection coil 30 side. For example, it is assumed that the work piece 15 is a component that has a shaft portion protruding from a predetermined proximal portion and a coupled portion between the proximal portion and the shaft portion is a measurement portion. In this case, the eddy current sensor is set to the work piece 15 in a state where the shaft portion is inserted from the detection coil 30 side through the through hole 23a of the first housing 23 (and the through hole 33a of the second housing 33). Then, the eddy current sensor is brought close to the coupled portion between the proximal portion and the shaft portion from the detection coil 30 side to thereby conduct eddy current measurement on the coupled portion. In this way, the eddy current sensor is used to conduct eddy current measurement to thereby inspect the quenching quality of the coupled portion of the work piece 15.

With the eddy current sensor according to the present embodiment, in the excitation coil 20, it is possible to enhance an exciting magnetic field as a synergistic effect caused by the interaction between the adjacent solenoid coils 21. By so doing, it is possible to easily obtain sufficiently strong magnetic fields in eddy current measurement.

In addition, in the excitation coil 20, a revolving magnetic field is generated between the adjacent solenoid coils 21, so it is possible to utilize the total of both the vertical magnetic fields (Hz) and the horizontal magnetic fields (Hx or Hy) for measurement. By so doing, the respective features of the vertical magnetic field (Hz) and the horizontal magnetic field (Hx or Hy) are, utilized, so it is possible to widen the width of variation in magnetic field identified through eddy current measurement, and it is possible to extend the range of application of eddy current measurement. Particularly, it is advantageous that an exciting magnetic field of the horizontal magnetic field (Hx or Hy) that receives relatively small influence of a distance between the measurement portion of the work piece 15 and the excitation coil 20 and that has a relatively low strength of magnetic field may be enhanced by a revolving magnetic field.

In addition, in the eddy current sensor according to the present embodiment, the plurality of solenoid coils 21 are arranged annularly, so it is possible to equalize variations in distance between the excitation coil 20 and the measurement portion of the work piece 15.

In addition, in the eddy current sensor according to the present embodiment, the detection coil 30 is formed so that the pancake coils 31 sensitive to a vertical magnetic field (Hz) and the horizontal solenoid coils 32 sensitive to a horizontal magnetic field (Hx or Hy), including the winding directions, are alternately arranged and coupled. By so doing, it is possible to enhance the detection sensitivity of the detection coil 30 and improve the detection efficiency of the detection coil 30.

In addition, the pancake coils 31 and horizontal solenoid coils 32 that constitute the detection coil 30, as in the case of the solenoid coils 21 that constitute the excitation coil 20, are arranged annularly, so it is possible to equalize variations in distance between the detection coil 30 and the measurement portion of the work piece 15.

Note that, in the eddy current sensor according to the present embodiment, the pancake coils 31 and horizontal solenoid coils 32 of the detection coil 30 are formed of a single continuous lead wire; however, the aspect of the invention is not limited to this configuration. That is, the pancake coils 31 and horizontal solenoid coils 32 that constitute the detection coil 30 may be respectively formed of separate lead wires, each coupling the pancake coils 31 or the horizontal solenoid coils 32. In addition, the pancake coils 31 and the horizontal solenoid coils 32 that are respectively formed of separate lead wires may have a multi-layer structure such that both coils are overlapped in the coil central axis direction on one side of the excitation coil 20 in the coil central axis direction. Here, when the detection coil 30 is formed of separate lead wires, the coils formed of the respective lead wires are connected to separate measuring units (measurement devices), respectively.

In addition, in the eddy current sensor according to the present embodiment, the first housing 23 (and the second housing 33) that constitutes the eddy current sensor has a revolver shape; however, the shape of the first housing 23 (and the second housing 33) is not limited to the revolver shape. That is, the shape of the outer peripheral portion of the housing that constitutes the eddy current sensor may be, for example, a simple cylindrical shape, a prism shape, or the like.

In addition, in the eddy current sensor according to the present embodiment, the detection coil 30 may include any one of the pancake coils 31 and the horizontal solenoid coils 32. That is, the eddy current sensor according to a first alternative configuration of the first embodiment may have a configuration such that the detection coil 30 includes any one of the pancake coils 31 and the horizontal solenoid coils 32 to thereby detect any one of the vertical magnetic field (Hz) and the horizontal magnetic field (Hx or Hy) (hereinafter, referred to as "unidirectional detection configuration").

Figure 7A:
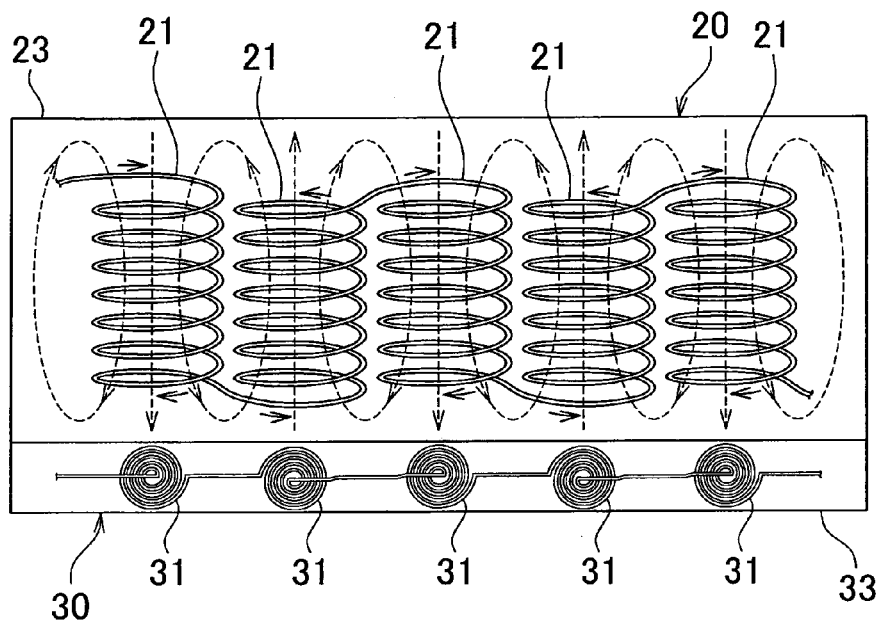
FIG. 7A is a view that shows a first alternative configuration of the eddy current sensor according to the first embodiment of the invention.
Figure 7B:
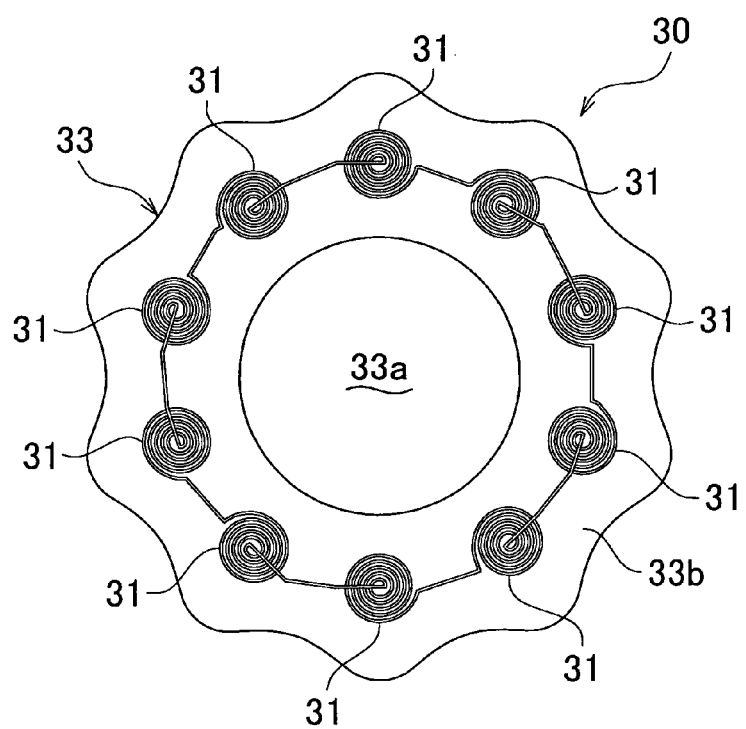
FIG. 7B is a view that shows the configuration of a detection coil in the first alternative configuration of the eddy current sensor according to the first embodiment of the invention.

In the unidirectional detection configuration, when the detection coil 30 includes only the pancake coils 31, the eddy current sensor is configured, for example, as shown in FIG. 7A and FIG. 7B. That is, in this case, as shown in FIG. 7A and FIG. 7B, the plurality of (ten in this embodiment) pancake coils 31 are arranged so as to be sensitive to a vertical magnetic field (Hz) with respect to the solenoid coils 21 that constitute the excitation coil 20, and are arranged and coupled annularly so that the winding directions are alternate.

That is, in this case, a single continuous lead wire is wound so that the winding directions are alternately arranged and the adjacent pancake coils 31 are coupled to each other. By so doing, the plurality of coupled pancake coils 31 are formed. In this way, when the detection coil 30 has a coupled structure of only the pancake coils 31, the eddy current sensor has a configuration exclusive to detection of a vertical magnetic field (Hz). Note that, for the sake of convenience, FIG. 7A shows the pancake coils 31 so that the central axes of the pancake coils 31 that are actually aligned along the central axes of the solenoid coils 21 (vertical direction) are perpendicular to the sheet (the same applies to FIG. 9 to FIG. 13 and FIG. 16 to FIG. 20).

Figure 8A:
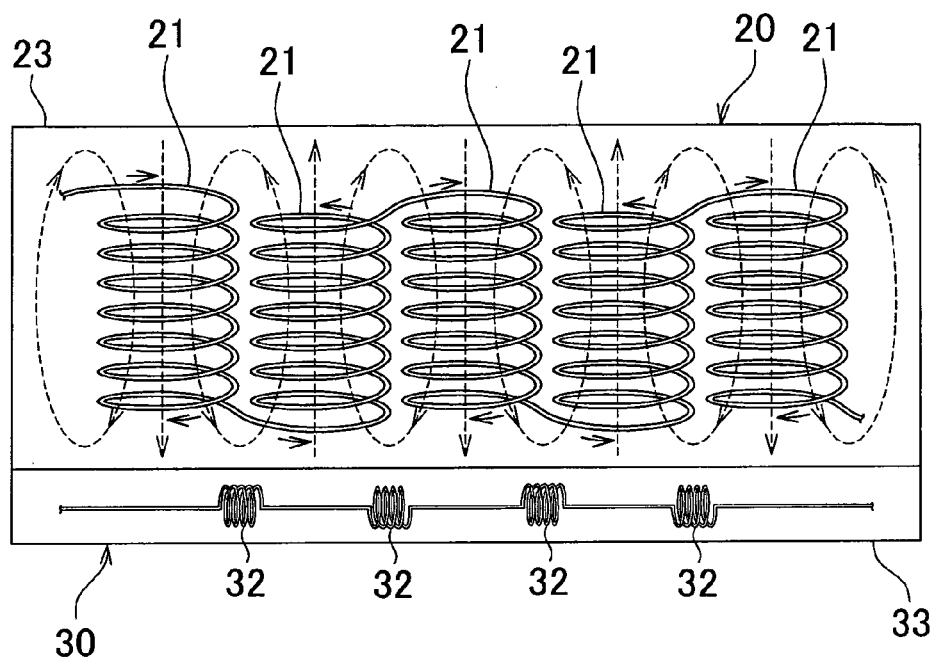
FIG. 8A is a view that shows a second alternative configuration of the eddy current sensor according to the first embodiment of the invention.
Figure 8B:
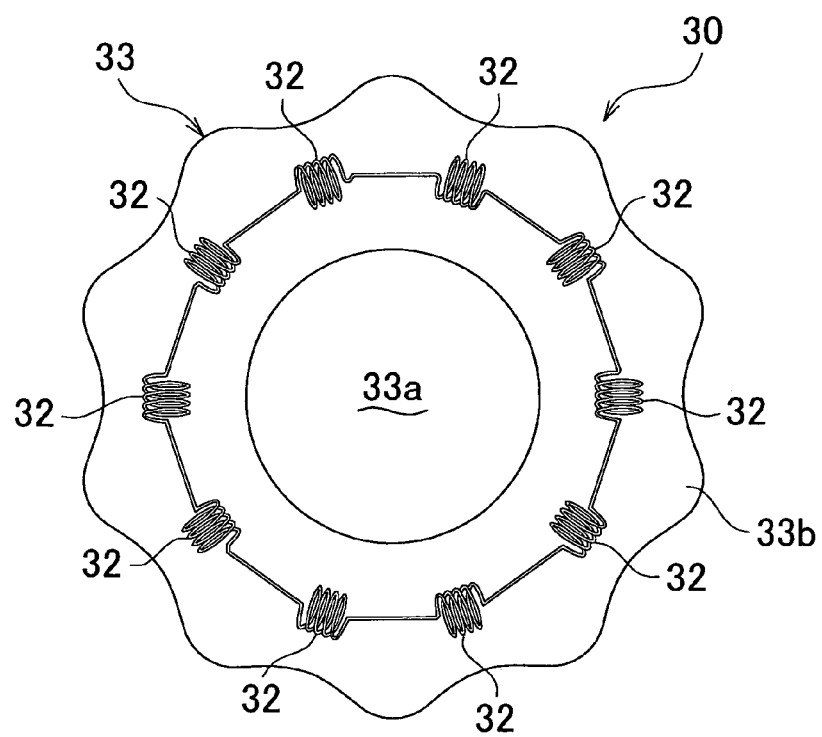
FIG. 8B is a view that shows the configuration of a detection coil in the second alternative configuration of the eddy current sensor according to the first embodiment of the invention.

In addition, in the unidirectional detection configuration, when the detection coil 30 includes only the horizontal solenoid coils 32, the eddy current sensor is configured, for example, as shown in FIG. 8A and FIG. 8B. That is, in this case, as shown in FIG. 8A and FIG. 8B, the plurality of (ten in this embodiment) horizontal solenoid coils 32 are arranged so as to sensitive to a horizontal magnetic field (Hx or Hy) with respect to the solenoid coils 21 that constitute the excitation coil 20, and are arranged and coupled annularly so that the winding directions are alternate.

That is, in this case, a single continuous lead wire is wound so that the winding directions are alternately arranged and the adjacent horizontal solenoid coils 32 are coupled to each other. By so doing, the plurality of coupled horizontal solenoid coils 32 are formed. In this way, when the detection coil 30 has a coupled structure of only the horizontal solenoid coils 32, the eddy current sensor has a configuration exclusive to detection of a horizontal magnetic field (Hx or Hy).

As described above, in the eddy current sensor according to the present embodiment, the detection coil 30 may include at least any one of the pancake coils 31 for detecting a vertical magnetic field (Hz) and the horizontal solenoid coils 32 for detecting a horizontal magnetic field (Hx or Hy).

Then, with the configuration (see FIG. 4 and FIG. 6) that the detection coil 30 has two types of coils, that is, the pancake coils 31 and the horizontal solenoid coils 32, it is possible to detect both a vertical magnetic field (Hz) and a horizontal magnetic field (Hx or Hy). The above configuration is employed, for example, when it is desired to detect variations in magnetic fields as much as possible for the work piece 15.

In addition, within the unidirectional detection configuration, with the configuration that the detection coil 30 includes only the pancake coils 31 (see FIG. 7A and FIG. 7B), it is possible to detect only a vertical magnetic field (Hz). The above configuration is employed, for example, when it is desired to use the eddy current sensor similarly to a normal probe-type sensor (see the probe-type coil 120 shown in FIG. 21B). That is, the vertical magnetic field (Hz) is relatively susceptible to a distance from the work piece 15. From the above, the configuration that the detection coil 30 has only the pancake coils 31 is employed, for example, in detection of cracks, which has a relatively high S/N ratio for a measured value and which is generally conducted using a probe-type sensor.

In addition, within the unidirectional detection configuration, with the configuration (see FIG. 8A and FIG. 8B) that the detection coil 30 has only the horizontal solenoid coils 32, it is possible to detect only a horizontal magnetic field (Hx or Hy). The above configuration is employed, for example, when a variation in distance between the eddy current sensor and the work piece 15 is relatively large. That is, the horizontal magnetic field (Hx or Hy) is relatively insusceptible to a distance from the work piece 15, and is robust against a distance from the work piece 15. That is, the horizontal magnetic field (Hx or Hy) is insusceptible to foreign matter, or the like, present on the surface of the work piece 15. From the above, the configuration that the detection coil 30 has only the horizontal solenoid coils 32 is employed, for example, in inspection of surface texture, such as inspection of quenching quality, which has a relatively small S/N ratio for a measured value.

In addition, in the eddy current sensor according to the present embodiment, the detection coil 30 may be detachable with respect to the excitation coil 20. In a third alternative configuration of the first embodiment, the configuration that the detection coil 30 is detachable with respect to the excitation coil 20 (hereinafter, referred to as "detachable configuration") is implemented in such a manner that the second housing 33 that supports the pancake coils 31 and horizontal solenoid coils 32 of the detection coil 30 are detachable with respect to the first housing 23 that supports the solenoid coils 21 of the excitation coil 20.

That is, in the detachable configuration, the second housing 33 of the detection coil 30 is configured to be attachable to and detachable from the first housing 23 of the excitation coil 20. Then, the second housing 33 of the detection coil 30 is attached to the first housing 23 of the excitation coil 20, so both housings 23 and 33 are integrated, and the excitation coil 20 and the detection coil 30 are assembled as the eddy current sensor. In addition, the second housing 33 of the detection coil 30 is detached from the first housing 23 of the excitation coil 20, so the excitation coil 20 and the detection coil 30 are separated from each other.

The configuration for attaching and detaching the first housing 23 of the excitation coil 20 to and from the second housing 33 of the detection coil 30 is not specifically limited as long as it is possible to easily attach and detach the second housing 33 of the detection coil 30 to and from the first housing 23 of the excitation coil 20. The configuration for attaching and detaching both housings 23 and 33, for example, includes a configuration that uses a fastening device, such as a bolt, a chuck mechanism that allows attaching and detaching with a single motion, and a fit that maintains an integral state of both housings 23 and 33.

In this way, when the detachable configuration is employed in the eddy current sensor according to the present embodiment, the detection coil 30 is supported by the second housing 33 that is a member detachable from the first housing 23 that is a member that supports the plurality of solenoid coils 21. Then, in the eddy current sensor having the detachable configuration, an independent two-layer structure is implemented in which the excitation coil 20 and the detection coil 30 are respectively formed as modules (an excitation module and a detection module).

Thus, with the detachable configuration for the eddy current sensor according to the present embodiment, it is possible to replace part of the detection coil 30 in accordance with the purpose, application, and the like, of eddy current measurement conducted using the eddy current sensor. Specifically, as shown in FIG. 9, for example, a first detection coil 30A, a second detection coil 30B and a third detection coil 30C that are respectively configured as the above described three types of detection coils 30 (detection modules) are prepared for one excitation coil 20 (excitation module).

Figure 9:
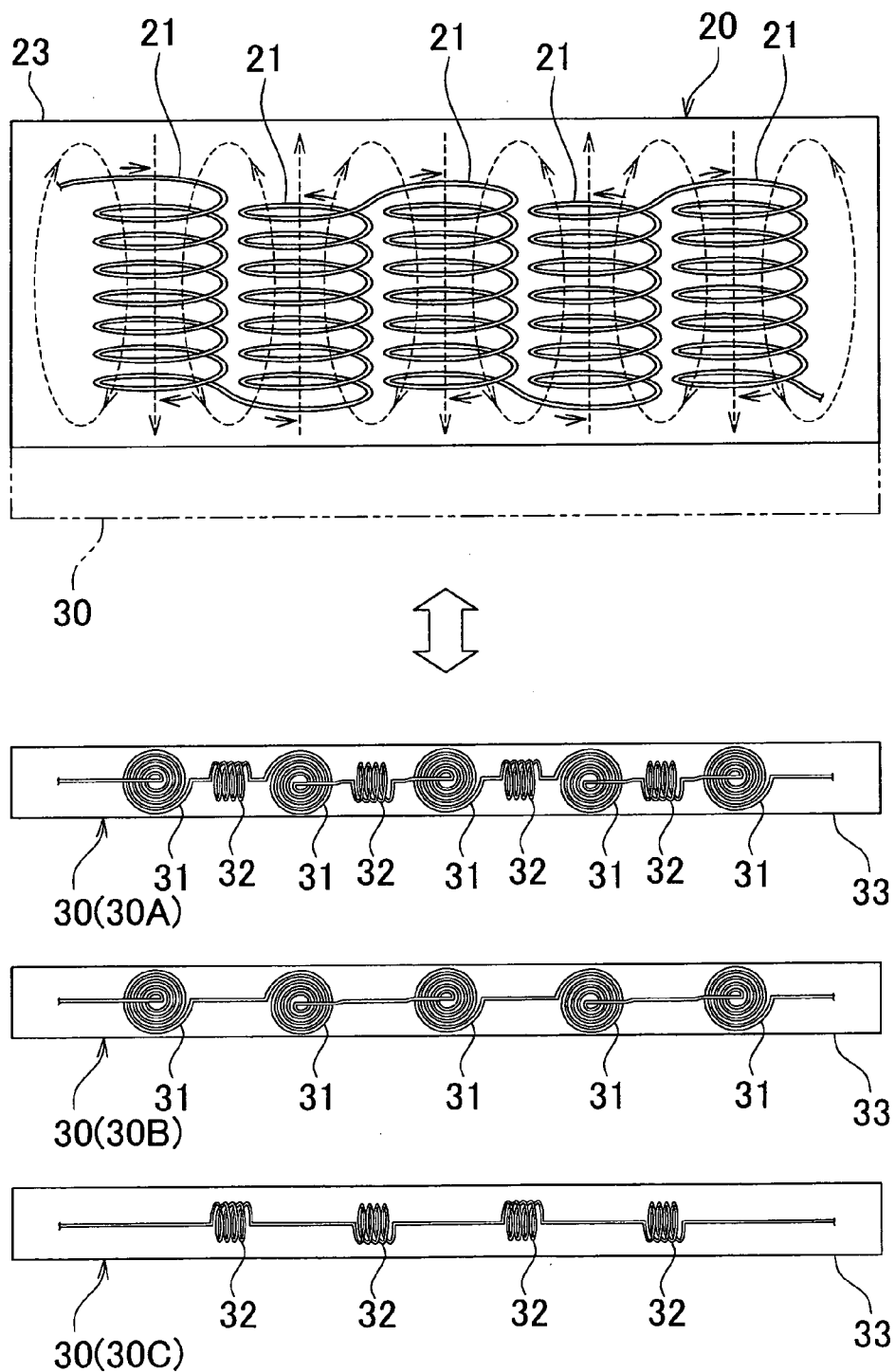
FIG. 9 is a view that shows a third alternative configuration of the eddy current sensor according to the first embodiment of the invention.

That is, in this case, as shown in FIG. 9, the first detection coil 30A is a detection coil 30 that has the pancake coils 31 and the horizontal solenoid coils 32, and is a detection module that is able to detect a vertical magnetic field (Hz) and a horizontal magnetic field (Hx or Hy) at the same time. In addition, the second detection coil 3013 is a detection coil 30 that has only the pancake coils 31, and is a detection module exclusive for a vertical magnetic field (Hz). In addition, the third detection coil 30C is a detection coil 30 that has only the horizontal solenoid coils 32, and is a detection module exclusive for a horizontal magnetic field (Hx or Hy).

Then, any one of the detection coils 30 (detection modules) is used in accordance with the purpose, application, and the like, of eddy current measurement conducted using the eddy current sensor. That is, any one of the detection coils 30 (detection modules), that is, the first detection coil 30A, the second detection coil 30B and the third detection coil 30C, is attached on one side (lower side) of the excitation coil 20 (excitation module). By so doing, the eddy current sensor in conformity with the purpose, application, and the like, of eddy current measurement is appropriately configured.

In addition, in the detachable configuration, the detection coil 30 is attached to the excitation coil 20 in correspondence with magnetic fields formed by the plurality of solenoid coils 21 of the excitation coil 20. That is, the detection coil 30 is attached to the excitation coil 20 in a state where the second housing 33 is positioned in correspondence with magnetic fields in the excitation coil 20 in the circumferential direction with respect to the first housing 23 of the excitation coil 20.

Specifically, when the detection coil 30 has the pancake coils 31, the detection coil 30 is positioned in the circumferential direction with respect to the excitation coil 20 so that the pancake coil 31 of which the winding direction corresponds to the direction of the vertical magnetic field (Hz) formed in each solenoid coil 21 is located coaxially with that solenoid coil 21. In addition, when the detection coil 30 has the horizontal solenoid coils 32, the detection coil 30 is positioned in the circumferential direction with respect to the excitation coil 20 so that the central axis of the horizontal solenoid coil 32 of which the winding direction corresponds to the direction of the horizontal magnetic field (Hx or Hy) formed between the adjacent solenoid coils 21 substantially coincides with the direction in which those adjacent solenoid coils 21 are arranged side by side.

The revolver shapes of the housings 23 and 33 of the respective excitation coil 20 and detection coil 30 are utilized for positioning the detection coil 30 in the circumferential direction with respect to the excitation coil 20. That is, in the excitation coil 20 in which the outer peripheral portion 23b of the first housing 23 has a wavy shape that is formed along the outer shapes of the solenoid coils 21 arranged annularly as described above, the arrangement of the plurality of solenoid coils 21, that is, the distribution of the vertical magnetic fields (Hz) and the horizontal magnetic fields (Hx or Hy) formed in the excitation coil 20, may be easily identified by the outer shape of the excitation coil 20. In addition, as in the case of the excitation coil 20, the detection coil 30 also has the second housing 33 of which the outer peripheral portion 33b has a wavy shape that is formed along the outer shapes of the solenoid coils 21 arranged annularly.

Then, the fact that "the wavy shapes of the outer peripheral portions 23b and 33b coincide with each other in the circumferential direction of the housings 23 and 33 of the respective excitation coil 20 and detection coil 30" is used as a guide to a state where the detection coil 30 is positioned in the circumferential direction with respect to the excitation coil 20. By so doing, in the detachable configuration, it is possible to obtain the accuracy of arrangement of the detection coil 30 with respect to the excitation coil 20, and it is possible to ease replacement work of the detection coil 30 that serves as a detection module. Note that positioning criteria that are separately provided for the housings 23 and 33, and the like, are, where necessary, used for the correspondence relationship between the winding directions of the pancake coils 31 and horizontal solenoid coils 32 and the magnetic fields formed in the excitation coil 20.

In addition, in the detachable configuration, the plurality of detection coils 30 (detection modules) of different types or the same type may be stacked on one side of the excitation coil 20 in the coil central axis direction. That is, in the eddy current sensor according to the present embodiment, the second housing 33 of the detection coil 30, which is a member detachable with respect to the first housing 23 of the excitation coil 20, may be a member stacked on the first housing 23 of the excitation coil 20.

In the eddy current sensor according to the present embodiment, when the configuration that the second housing 33 of the detection coil 30 is stacked on the first housing 23 of the excitation coil 20 (hereinafter, "stacking configuration") is employed, the eddy current sensor may be, for example, configured as follows (fourth alternative configuration).

Figure 10:
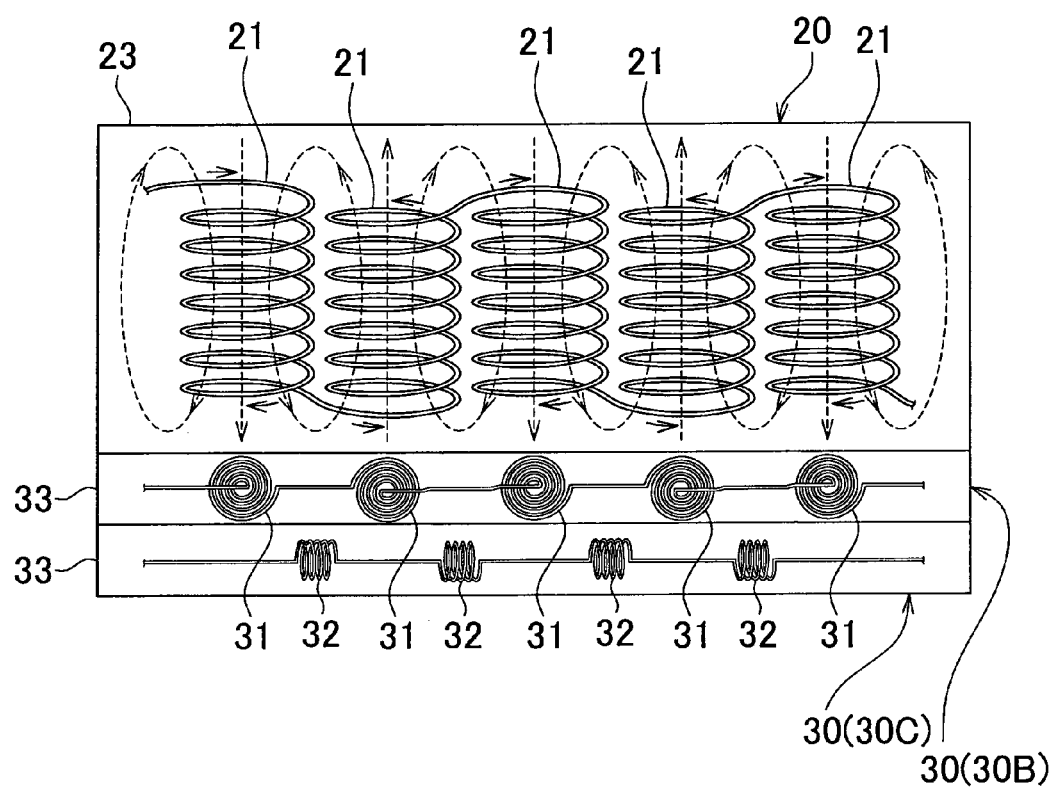
FIG. 10 is a view that shows a fourth alternative configuration of the eddy current sensor according to the first embodiment of the invention.

That is, as shown in FIG. 10, in the present alternative configuration, among the above described three types of detection coils 30 (detection modules), the second detection coil 30B having only the pancake coils 31 and the third detection coil 30C having only the horizontal solenoid coils 32 are stacked on one side (lower side) of the excitation coil 20 in the coil central axis direction.

Specifically, the second housing 33 of the second detection coil 30B is attached to one side of the first housing 23 of the excitation coil 20 in the coil central axis direction, and the third detection coil 30C is attached so as to be stacked on the second detection coil 30B. That is, the second housing 33 of the second detection coil 30B is attached so as to be sandwiched between the first housing 23 of the excitation coil 20 and the second housing 33 of the third detection coil 30C.

Thus, in the stacking configuration, the stacked second housings 33 of the detection coils 30 are detachable from each other. The configuration for attaching and detaching the second housings 33 of the detection coils 30 to and from each other is not specifically limited as in the case of the relationship between the first housing 23 of the excitation coil 20 and the second housing 33 of the detection coil 30 in the above described detachable configuration. For example, a configuration that uses a fixture, such as a bolt, is employed where necessary.

With the stacking configuration of the eddy current sensor according to the present embodiment, the advantageous effect in terms of cost may be expected. That is, with the stacking configuration of the second detection coil 30B having only the pancake coils 31 and the third detection coil 30C having only the horizontal solenoid coils 32 as shown in FIG. 10, detection signals from the respective detection coils 30 are synthesized to thereby make it possible to obtain a detection signal substantially similar to a detection signal obtained from the configuration (see the first detection coil 30A) in which the pancake coils 31 and the horizontal solenoid coils 32 are alternately arranged and coupled. In addition, the configuration of the detection coil 30 that has only any one of the pancake coils 31 and the horizontal solenoid coils 32 is lower in cost than the configuration of the detection coil 30 that has the pancake coils 31 and the horizontal solenoid coils 32 that are alternately arranged and coupled.

Thus, with the stacking configuration of the second detection coil 30B having only the pancake coils 31 and the third detection coil 30C having only the horizontal solenoid coils 32, it is possible to obtain a similar function to that of the detection coil 30 (first detection coil 30A) having both the pancake coils 31 and the horizontal solenoid coils 32 at a relatively low cost. However, in the stacking configuration of the eddy current sensor according to the present embodiment, the number, type, or the like, of the stacked detection coils 30 is not specifically limited.

In addition, in the eddy current sensor according to the present embodiment, the detection coils 30 may be provided on vertically both sides of the excitation coil 20. That is, in the eddy current sensor that serves as fifth to seventh alternative configurations of the first embodiment, the detection coils 30 may be arranged on both sides of the excitation coil 20 in the coil central axis direction.

In the eddy current sensor according to the present embodiment, when the configuration that the detection coils 30 are arranged on both sides of the excitation coil 20 in the coil central axis direction (hereinafter, referred to as "both-sides arrangement configuration") is employed, for example, a combination of different two types among the above described three types of detection coils 30 is used.

Specifically, when different two types of detection coils 30 are used in the both-sides arrangement configuration, the eddy current sensor may be configured as the following three configurations. In the first configuration (fifth alternative configuration), as shown in FIG. 11A, a vertical and horizontal detection coil 30D, which is the detection coil 30 having the configuration that the pancake coils 31 and the horizontal solenoid coils 32 are alternately arranged and coupled, is arranged on one side (lower side) of the excitation coil 20 in the coil central axis direction, and a vertical detection coil 30E, which is the detection coil 30 having only the pancake coils 31, is arranged on the other side (upper side) of the excitation coil 20 in the coil central axis direction.

In the second configuration (sixth alternative configuration), as shown in FIG. 11B, the vertical and horizontal detection coil 30D is arranged on one side (lower side) of the excitation coil 20 in the coil central axis direction, and a horizontal detection coil 30F, which is the detection coil 30 having only the horizontal solenoid coils 32, is arranged on the other side (upper side) of the excitation coil 20 in the coil central axis direction. In the third configuration (seventh alternative configuration), as shown in FIG. 11C, the vertical detection coil 30E is arranged on one side (lower side) of the excitation coil 20 in the coil central axis direction, and the horizontal detection coil 30F is arranged on the other side (upper side) of the excitation coil 20 in the coil central axis direction.

Then, any one of the detection coils 30 of each eddy current sensor is used in accordance with the purpose, application, and the like, of eddy current measurement conducted using the eddy current sensor. That is, between (two type) detection coils 30 on both sides of the eddy current sensor, the detection coil 30 that is brought close to the work piece 15 is switched (reversed) where necessary in accordance with the purpose, application, and the like, of eddy current measurement. In this way, with the both-sides arrangement configuration according to the present embodiment, the single eddy current sensor may include two types of detection coils 30, so it is possible to improve the efficiency of work in eddy current measurement.

As described above, in the eddy current sensor according to the present embodiment, it is only necessary that the detection coil 30 is arranged at least on one side between the two sides of the excitation coil 20 in the coil central axis direction. Note that, in the both-sides arrangement configuration, the configuration that the detection coils 30 of the same type are arranged on the excitation coil 20 (for example, a configuration that the vertical and horizontal detection coil 30D is arranged on each side in the coil central axis direction) may be employed. In addition, in the both-sides arrangement configuration, the above described detachable configuration may be employed.

In addition, in the eddy current sensor according to the present embodiment, the plurality of solenoid coils 21 that are arranged annularly in the excitation coil 20 may be arranged at an angle so as to converge at the detection coil 30 side in accordance with the shape of the measurement portion of the work piece 15. That is, in the eddy current sensor according to an eighth alternative configuration of the present embodiment, the plurality of solenoid coils 21 may be arranged in a state where ends of the plurality of solenoid coils 21 on the same side in the coil central axis direction are inclined toward the inner side of a ring formed of the plurality of solenoid coils 21 arranged annularly (ring that is the shape of arrangement of the plurality of solenoid coils 21; the same applies to the following description).

Figure 12:
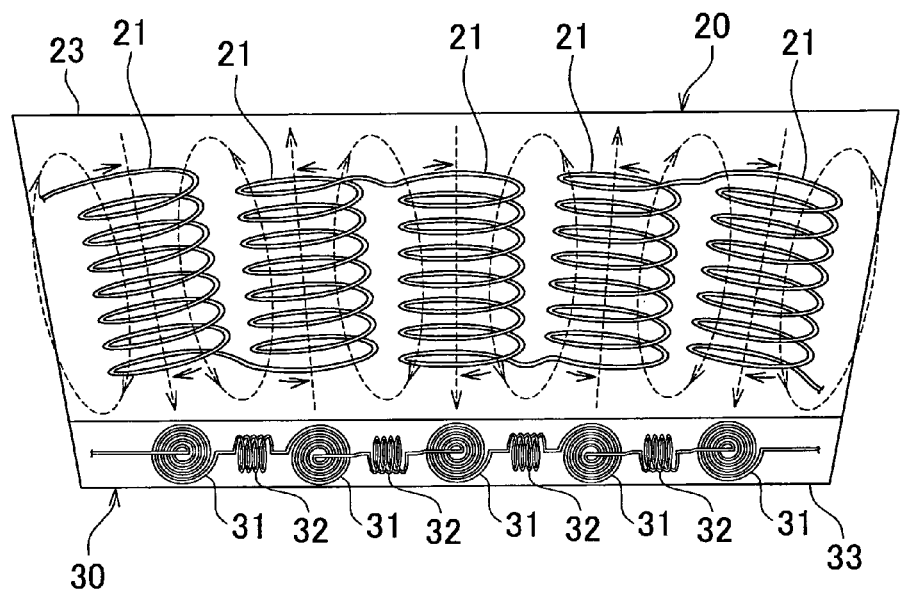
FIG. 12 is a view that shows an eighth alternative configuration of the eddy current sensor according to the first embodiment of the invention.

In the eddy current sensor according to the present embodiment, when the configuration that the plurality of solenoid coils 21 that constitute the excitation coil 20 are arranged in a state where the plurality of solenoid coils 21 are inclined in accordance with the shape of the work piece 15 (hereinafter, referred to as "inclined configuration") is employed, it may be, for example, the configuration shown in FIG. 12.

That is, as shown in FIG. 12, in the inclined configuration, the plurality of solenoid coils 21 that constitute the excitation coil 20 are arranged at an angle with respect to the central axis of the ring (vertical direction in FIG. 12) so that ends on the same side (lower sides in FIG. 12) in the coil central axis direction are directed inwardly of the ring (center side of the ring).

In this way, in the inclined configuration, the plurality of solenoid coils 21 are arranged so that the ring formed by the arrangement of the plurality of solenoid coils 21 forms a substantially cone shape that reduces in diameter toward the detection coil 30 (lower side in FIG. 12). Thus, when the inclined, configuration is employed in the eddy current sensor according to the present embodiment, the solenoid coils 21 are arranged side by side in a state where the coil central axes are inclined with respect to the vertical direction. Then, in the inclined configuration, the pancake coils 31 and horizontal solenoid coils 32 that constitute the detection coil 30 are appropriately arranged in correspondence with the directions of the magnetic fields formed by the plurality of solenoid coils 21 arranged in an inclined manner.

Figure 21A:
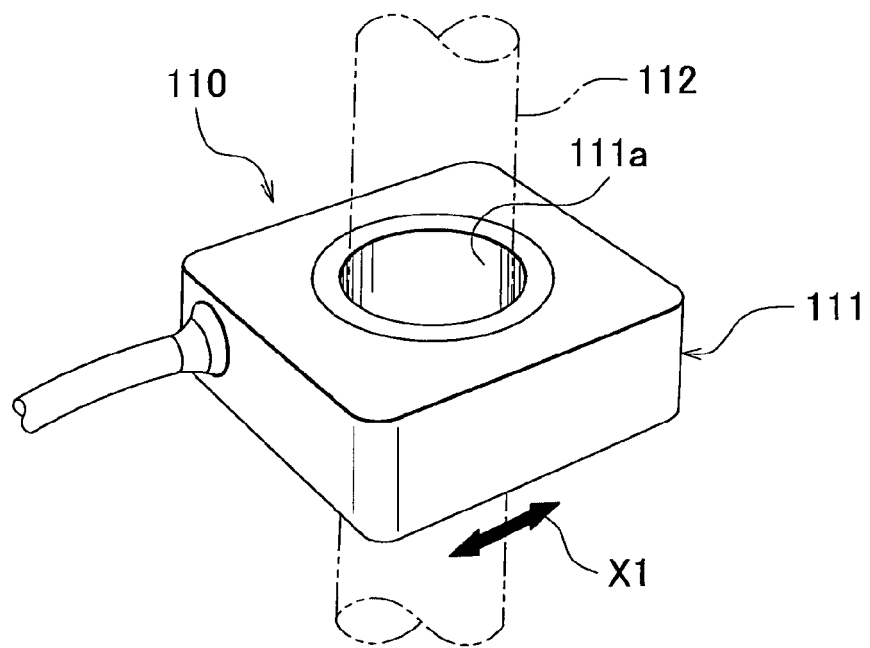
FIG. 21A is a view that shows the configuration of an eddy current sensor according to a related art regarding a through-type coil.

With the inclined configuration of the eddy current sensor according to the present embodiment, by, for example, adjusting the angle at which each solenoid coil 21 is inclined, it is possible to cause the magnetic fields excited by the excitation coil 20 to converge at a desired portion in eddy current measurement. By so doing, for example, it is possible to easily conduct eddy current measurement on a curved portion formed between the shaft portion and the proximal portion, for which it has been difficult to conduct eddy current measurement using the existing through-type coil (see the through-type coil 110 shown in FIG. 21A).

Here, an example of a component having a curved portion may be an CVJ outer race. The CVJ outer race is a component that constitutes a constant velocity joint (CVJ). The CVJ outer race is generally a component quenched by means of induction quenching, or the like. Then, when the work piece 15 is a CVJ outer race, the eddy current sensor having an inclined configuration is used as follows.

Figure 13:
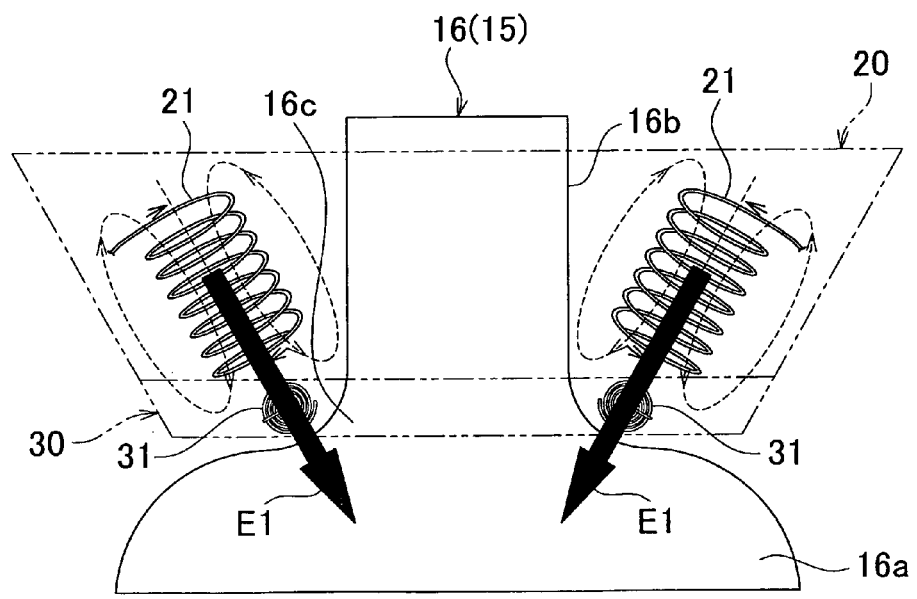
FIG. 13 is a view that shows an application example of the eighth alternative configuration of the eddy current sensor according to the first embodiment of the invention.

That is, as shown in FIG. 13, the CVJ outer race 16, which is the work piece 15, has a cup portion 16a and a joint portion 16b. The cup portion 16a is a large-diameter portion (proximal portion). The joint portion 16b is a shaft portion and is provided on the upper side of the cup portion 16a. Then, in the CVJ outer race 16, a curved portion 16c is a coupled portion between the cup portion 16a and the joint portion 16b, that is, a portion of the joint portion 16b connected to the cup portion 16a.

In this way, the eddy current sensor is set to the CVJ outer race 16 having the curved portion 16c in a state where the joint, portion 16b is inserted from the detection coil 30 side into the through hole 23a of the first housing 23 (and the through hole 33a of the second housing 33). Then, the detection coil 30 side is brought close to the curved portion 16c to conduct eddy current measurement on the curved portion 16c. In this way, the eddy current sensor is used to conduct eddy current measurement to thereby inspect the quenching quality of the curved portion 16c of the CVJ outer race 16.

As shown in FIG. 13, with the eddy current sensor having an inclined configuration, the plurality of solenoid coils 21 that constitute the excitation coil 20 are arranged so as to converge toward the curved portion 16c of the CVJ outer race 16. Thus, in the excitation coil 20, a magnetic field (vertical magnetic field (Hz)) that is formed in each solenoid coil 21 and that is aligned in the coil central axis direction is formed so as to be directed toward the curved portion 16c (see the arrows E1). In other words, in the eddy current sensor having an inclined configuration, the inclined angle, arrangement, and the like, of each solenoid coil 21 are set so that the directions of magnetic fields excited by the excitation coil 20 are directed toward the curved portion 16c.

In this way, the eddy current sensor having an inclined configuration is used, and eddy current measurement is conducted on the curved portion 16c of the CVJ outer race 16. By so doing, it is possible to cause the magnetic fields excited by the excitation coil 20 to converge at the curved portion 16c, and it is possible to improve the accuracy of measurement. That is, the inclined configuration is employed in the eddy current sensor, so it is possible to accurately conduct eddy current measurement on a portion for which it is desired to assure the quenching quality because the portion is applied with relatively large external stress in the quenched component as in the case of the curved portion 16c of the CVJ outer race 16.

With the above described eddy current sensor according to the present embodiment, it is possible to set a portion having a shape, other than a shaft portion of a shaft-like component, as a measurement target, and it is possible to extend the range of application of eddy current measurement. That is, in the eddy current sensor according to the present embodiment, sufficiently strong magnetic fields may be obtained by the interaction between the adjacent solenoid coils 21, and directivity may be imparted to the magnetic fields, so it is possible to obtain desired magnetic fields suitable for eddy current measurement by means of the arrangement, coupling method, and the like, of coils. By so doing, it is possible to implement wide-ranging eddy current measurement according to the type and shape of the work piece 15 or the purpose, application, and the like, of eddy current measurement. Then, in the eddy current sensor according to the present embodiment, by appropriately using the above described unidirectional detection configuration, detachable configuration, stacking configuration, both-sides arrangement configuration and inclined configuration, it is possible to further extend the range of application of eddy current measurement.

Note that the shape of arrangement of the solenoid coils 21 that constitute the excitation coil 20 is not limited to the annular shape described in the present embodiment. However, when the plurality of solenoid coils 21 are arranged annularly, these are arranged and coupled so that the winding directions are alternate, so the number of solenoid coils 21 of the excitation coil 20 is an even number.

In addition, in the eddy current sensor according to the present embodiment, instead of the pancake coils 31 used to detect a vertical magnetic field (Hz) in the detection coil 30, vertical solenoid coils, planar coils, or the like, may be employed. In this case, as in the case of the pancake coils 31, the vertical solenoid coils, the planar coils, or the like, are arranged so that the positions of the central axes substantially coincide with the positions of the central axes of the solenoid coils 21.

A second embodiment of the invention will be described. Note that like reference numerals denote similar components to those of the above described first embodiment of the invention, and the overlap description is omitted where appropriate. An eddy current sensor according to the present embodiment, as in the ease of the first embodiment, includes an excitation coil 40 and a detection coil 50. The excitation coil 40 is used to apply a predetermined alternating-current excitation signal to a work piece. The detection coil 50 is used to detect a detection signal, generated by eddy current, from the work piece to which the alternating-current excitation signal is applied.

Figure 14:
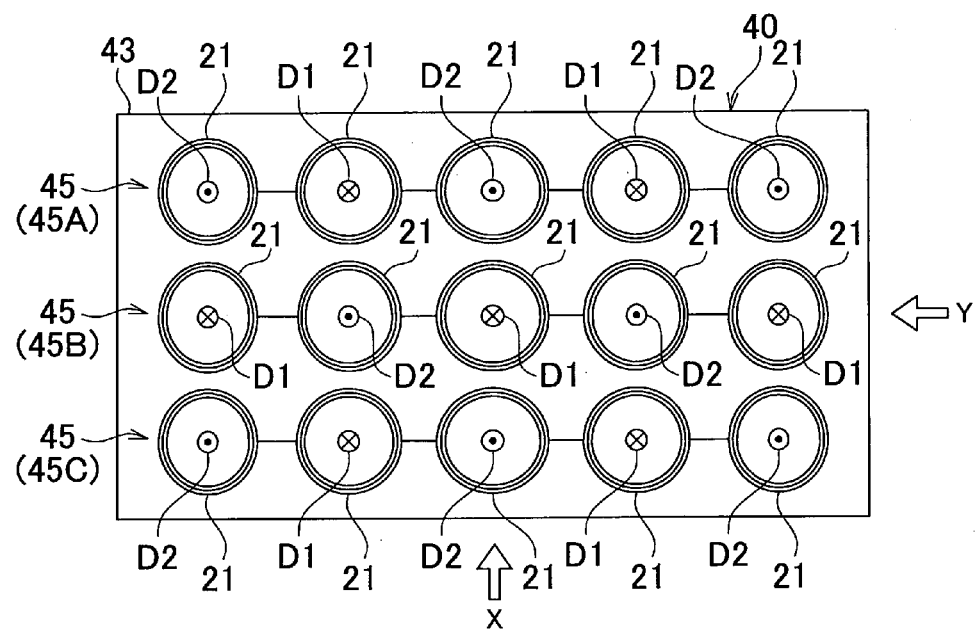
FIG. 14 is a view that shows the configuration of an excitation coil of an eddy current sensor according to a second embodiment of the invention.

As shown in FIG. 14, in the eddy current sensor according to the present embodiment, the excitation coil 40 has a plurality of coil rows 45. Each of the plurality of coil rows 45 includes the plurality of solenoid coils 21 arranged in a predetermined direction. The plurality of coil rows 45 may be separately applied with an alternating-current excitation signal. Each coil row 45 is formed of the plurality of solenoid coils 21. The plurality of solenoid coils 21 are arranged in a predetermined direction in parallel with one another so that the winding directions (directions in which electric current flows) are alternate.

In the present embodiment, the plurality of solenoid coils 21 that are arranged in the predetermined direction as each coil row 45 are arranged along substantially a straight line when viewed in the coil central axis direction (see FIG. 14) of any one of the solenoid coils 21 that constitute the coil row 45. In this way, in the present embodiment, the direction of the substantially straight line along which the plurality of solenoid coils 21 that constitute the coil row 45 (horizontal direction in FIG. 14) corresponds to the predetermined direction regarding the arrangement of the plurality of solenoid coils 21 that constitute the coil row 45. In the following description, the predetermined direction (horizontal direction in FIG. 14) in which the plurality of solenoid coils 21 that constitute the coil row 45 is referred to as "series direction".

In the present embodiment, each coil row 45 is formed of five solenoid coils 21. That is, in the present embodiment, each of the coil rows 45 is formed of five solenoid coils 21 that are arranged and coupled in the series direction. The five solenoid coils 21 are formed of a single continuous lead wire and are arranged in parallel with one another so that the winding directions are alternate.

In this way, the plurality of coil rows 45 of the excitation coil 40 are arranged side by side so that the winding directions of the adjacent solenoid coils 21 are alternate. In the present embodiment, the excitation coil 40 has three sets of the coil rows 45 that are arranged side by side in parallel with one another as shown in FIG. 14. That is, the five solenoid coils 21 are arranged in the series direction to form each coil row 45, and the three coil rows 45 are arranged; so the excitation coil 40 according to the present embodiment has fifteen solenoid coils 21 in total. In the following description, a direction (vertical direction in FIG. 14) in which three coil rows 45 are arranged in parallel with one another is referred to as "parallel direction".

In the present embodiment, three coil rows 45 are arranged so that the solenoid coils 21 that constitute the respective coil rows 45 are arranged in the parallel direction. That is, as shown in FIG. 14, the five solenoid coils 21 of each coil row 45 are present in a state where the positions in the series direction are aligned with respect to the positions of the solenoid coils 21 of the other coil rows 45. Thus, the fifteen solenoid coils 21 of the excitation coil 40 according to the present embodiment are regularly arranged (at substantially equal intervals) in the series direction and in the parallel direction.

Then, each coil row 45 is configured so that the winding directions of the three solenoid coils 21 arranged in the parallel direction are alternate between the adjacent coil rows 45. That is, the three coil rows 45 are arranged in a state where the winding directions of the corresponding (adjacent) solenoid coils 21 in the parallel direction are opposite. In other words, the three coil rows 45 are arranged in a state where the winding directions of the solenoid coils 21 that are closest to each other and that are side by side in the parallel direction are opposite between the adjacent coil rows 45.

That is, as shown in FIG. 14, when the three coil rows 45 of the excitation coil 40 are respectively termed as a first coil row 45A, a second coil row 45B and a third coil row 45C in order from the upper side in FIG. 14, between the first coil row 45A and the second coil row 45B, the corresponding (adjacent) solenoid coils 21 in the parallel direction have opposite winding directions. Similarly, between the second coil row 45B and the third coil row 45C as well, the corresponding (adjacent) solenoid coils 21 in the parallel direction have opposite winding directions. Note that, in FIG. 14, as in the case shown in FIG. 5 in the first embodiment, a marked portion indicated by the reference sign D1 or the reference sign D2 in each solenoid coil 21 indicates the direction of the vertical magnetic field of each solenoid coil 21.

In this way, the fifteen solenoid coils 21 of the excitation coil 40 are arranged so as to generate revolving magnetic fields by the interaction of the adjacent solenoid coils 21 in the series direction and in the parallel direction. That is, the fifteen solenoid coils 21 of the excitation coil 40 are arranged so as to reinforce the mutual magnetic fields between the adjacent solenoid coils 21 in the series direction and in the parallel direction.

The three coil rows 45 of the excitation coil 40 may be separately applied with an alternating-current excitation signal. That is, the excitation coil 40 according to the present embodiment is configured as a three-channel excitation coil that is able to set different excitation frequencies for alternating-current excitation signals in the respective three coil rows 45 (frequencies of alternating-current excitation signals). Thus, the three coil rows 45 of the excitation coil 40 are connected to separate power supply units (see the alternating-current power supply 10 in FIG. 2).

Figure 15:
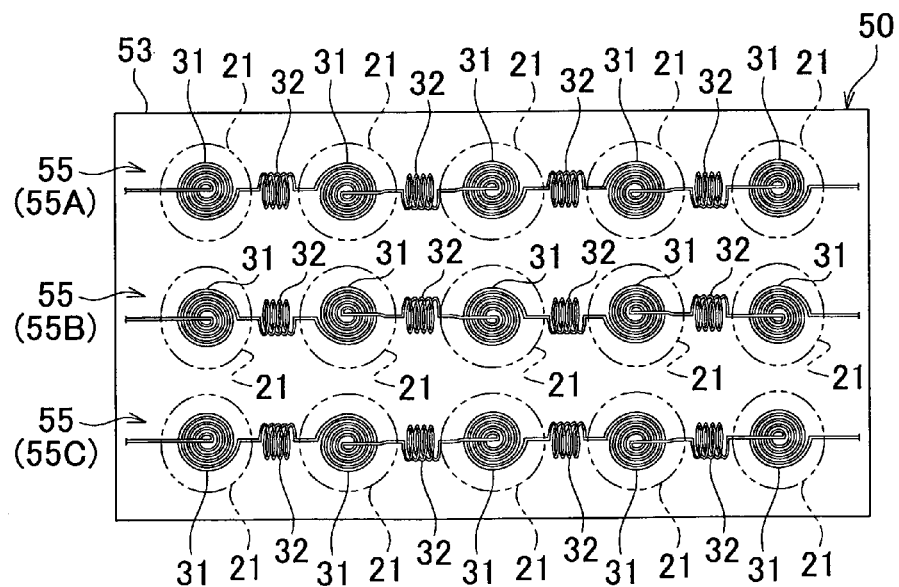
FIG. 15 is a view that shows the configuration of a detection coil according to the second embodiment of the invention.

As shown in FIG. 15, the detection coil 50 of the eddy current sensor according to the present embodiment has three sets of coil groups 55 provided in correspondence with the three coil rows 45 of the excitation coil 40. In addition, in the present embodiment, each coil group 55 has the pancake coils 31 and the horizontal solenoid coils 32.

That is, as shown in FIG. 15, the detection coil 50 includes a first coil group 55A, a second coil group 55B and a third coil group 55C. The first coil group 55A corresponds to the first coil row 45A of the excitation coil 40. Similarly, the second coil group 55B corresponds to the second coil row 45B. Similarly, the third coil group 55C corresponds to the third coil row 45C. Then, the pancake coils 31 and horizontal solenoid coils 32 that constitute each coil group 55 are arranged in correspondence with the directions of the magnetic fields formed by the solenoid coils 21 that constitute the corresponding coil row 45.

Thus, each coil group 55 of the detection coil 50 has five pancake coils 31 and four horizontal solenoid coils 32. The five pancake coils 31 are arranged so as to be coaxially located with respect to the solenoid coils 21 that constitute a corresponding one of the coil rows 45 of the excitation coil 40 (so that the positions of the central axes substantially coincide with each other). The four horizontal solenoid coils 32 are arranged so that the directions of the central axes coincide with the direction in which the adjacent solenoid coils 21 are arranged (series direction). Then, the pancake coils 31 and horizontal solenoid coils 32 that constitute each coil group 55 are formed of a single continuous lead wire so that the coils of different types are alternate and the winding directions of the coils of the same type are alternate, and are arranged and coupled in the series direction as in the case of the coil rows 45.

Each of the three coil groups 55 of the detection coil 50 is able to detect a detection signal independently. That is, the detection coil 50 according to the present embodiment is configured as a three-channel detection coil that uses the coil groups 55 to make it possible to detect detection signals corresponding to alternating-current excitation signals applied by the respective three coil rows 45 of the excitation coil 40. Thus, the three coil groups 55 of the detection coil 50 are connected to separate measuring units (see the measurement device 11 in FIG. 2).

In addition, the solenoid coils 21 (coil rows 45) that constitute the excitation coil 40 and the pancake coils 31 and horizontal solenoid coils 32 (coil groups 55) that constitute the detection coil 50 are supported in the above described arrangement and coupled state by a first housing 43 and a second housing 53 that are formed of resin members having predetermined shapes as in the case of the first embodiment. Then, when eddy current measurement is conducted using the eddy current sensor according to the present embodiment, the eddy current sensor is brought close to the measurement portion of the work piece from the detection coil 50 side.

With the thus configured eddy current sensor according to the present embodiment, because a three-channel mode is employed for the excitation coil 40, it is possible to carry out separate excitation using the respective channels (coil rows 45), that is, multiple excitation. By so doing, for example, when the measurement portion has a partially different quench depth because of the shape, or the like, of a work piece, each of the coil rows 45 in the single eddy current sensor is able to independently select and set the excitation frequency according to a quench depth for portions having different quench depths.

That is, regarding an alternating-current excitation signal generated by the eddy current sensor, as the excitation frequency decreases, the depth of penetration of eddy current to the work piece increases; whereas, as the excitation frequency increases, the depth of penetration of eddy current to the work piece decreases. Specifically, as shown in FIG. 1, regarding an alternating-current excitation signal generated by the eddy current sensor, for example, when the excitation frequency f is about 30 kHz, the depth of penetration reaches a slight portion of the surface of the hardened layer 1 formed in the surface side of the quenched component. In addition, when the excitation frequency f is about 30 Hz, the depth of penetration reaches the base layer 2 that is not influenced by quenching.

Thus, when eddy current measurement is used for inspecting quenching quality, the excitation frequency of each coil row 45 is appropriately set within the range of about 30 kHz to 30 Hz on the basis of the quench depth of the measurement portion. That is, the excitation frequency of the coil row 45 corresponding to a portion of which the quench depth is relatively shallow in the measurement portion is set to be relatively high; whereas, the excitation frequency of the coil row 45 corresponding to a portion of which the quench depth is relatively deep in the measurement portion is set to be relatively low.

In this way, with the eddy current sensor according to the present embodiment, the single eddy current sensor is able to select and set different excitation frequencies for the coil rows 45 on the basis of a partial difference in quench depth in the measurement portion of the work piece. By so doing, it is possible to conduct accurate eddy current measurement according to the quench depth as an inspection for quenching quality.

Figure 16:
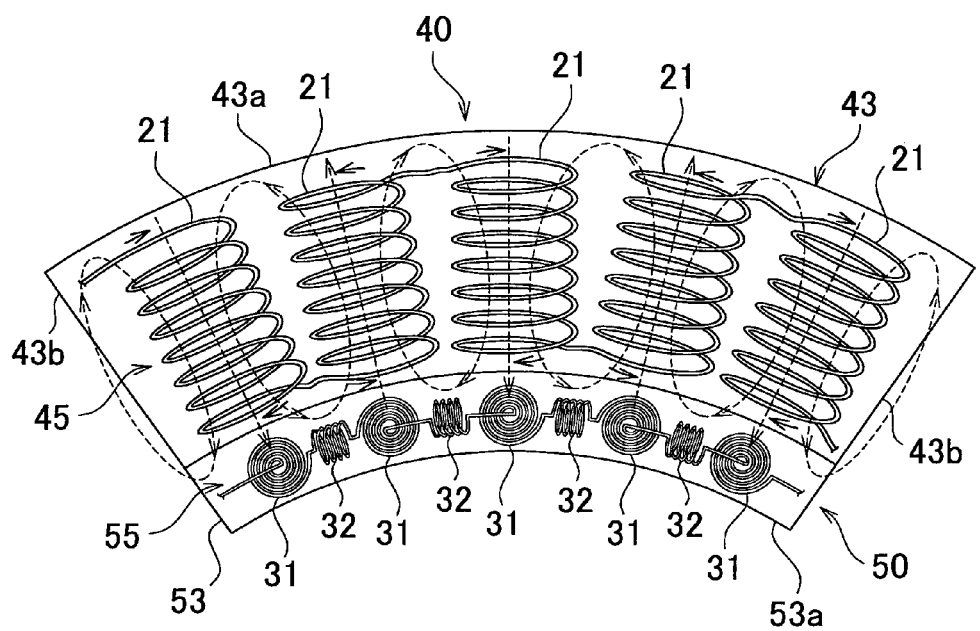
FIG. 16 is a view in the arrow X direction in FIG. 14.

In addition, the eddy current sensor according to the present embodiment has a substantially circular arc shape that is curved with respect to the series direction. That is, as shown in FIG. 16, in the eddy current sensor according to the present embodiment, each coil row 45 formed of the plurality of solenoid coils 21 arranged in the series direction is arranged so as to be curved, so the plurality of solenoid coils 21 are arranged in a substantially circular arc shape. That is, the coil central axes of the five solenoid coils 21 that constitute each coil row 45 of the excitation coil 40 are arranged so as to be directed toward the center of the circular arc.

The detection coil 50 is formed along a substantially circular arc shape (curved shape) in correspondence with the excitation coil 40 in which the five solenoid coils 21 that constitute each coil row 45 are arranged in a substantially circular arc shape. That is, the pancake coils 31 and horizontal solenoid coils 32 that constitute each coil group 55 in the detection coil 50 are arranged in a substantially circular arc shape along the substantially circular arc shape, which is the shape of arrangement of the solenoid coils 21 that constitute each coil row 45.

Then, in the eddy current sensor according to the present embodiment, the first housing 43 of the excitation coil 40 and the second housing 53 of the detection coil 50 are integrally formed, and have a substantially circular arc shape corresponding to the shape of arrangement of the coils in each coil row 45 and each coil group 55. That is, as shown in FIG. 16, the first housing 43 of the excitation coil 40 and the second housing 53 of the detection coil 50 are integrally formed as a single housing, and the housing forms a substantially circular arc shape with an outer peripheral surface 43*a* and inner peripheral surface 53*a* that are curved in the series direction and both side surfaces 43*b* in the series direction when viewed in the horizontal direction (when viewed in the X direction in FIG. 14).

As shown in FIG. 16, the outer peripheral surface 43*a* of the housing of the eddy current sensor according to the present embodiment is a surface of the first housing 43 of the excitation coil 40, opposite to the detection coil 50 side in the coil central axis direction. In addition, the inner peripheral surface 53*a* is a surface of the second housing 53 of the detection coil 50, opposite to the excitation coil 40 side in the coil central axis direction. In addition, each side surface 43*b* is a planar portion that is formed of end surface of the first housing 43 of the excitation coil 40 and the end surface of the second housing 53 of the detection coil 50 in the series direction.

In this way, with the eddy current sensor formed in a substantially circular arc shape including the shape of arrangement of the coils, it is possible to easily conduct eddy current measurement on a shaft portion that cannot be inserted through a hole, or the like, of the housing of the eddy current sensor because of the shape of a work piece. Here, the shaft portion that cannot be inserted through the eddy current sensor may be a journal portion or pin portion of a crankshaft.

Figure 19:
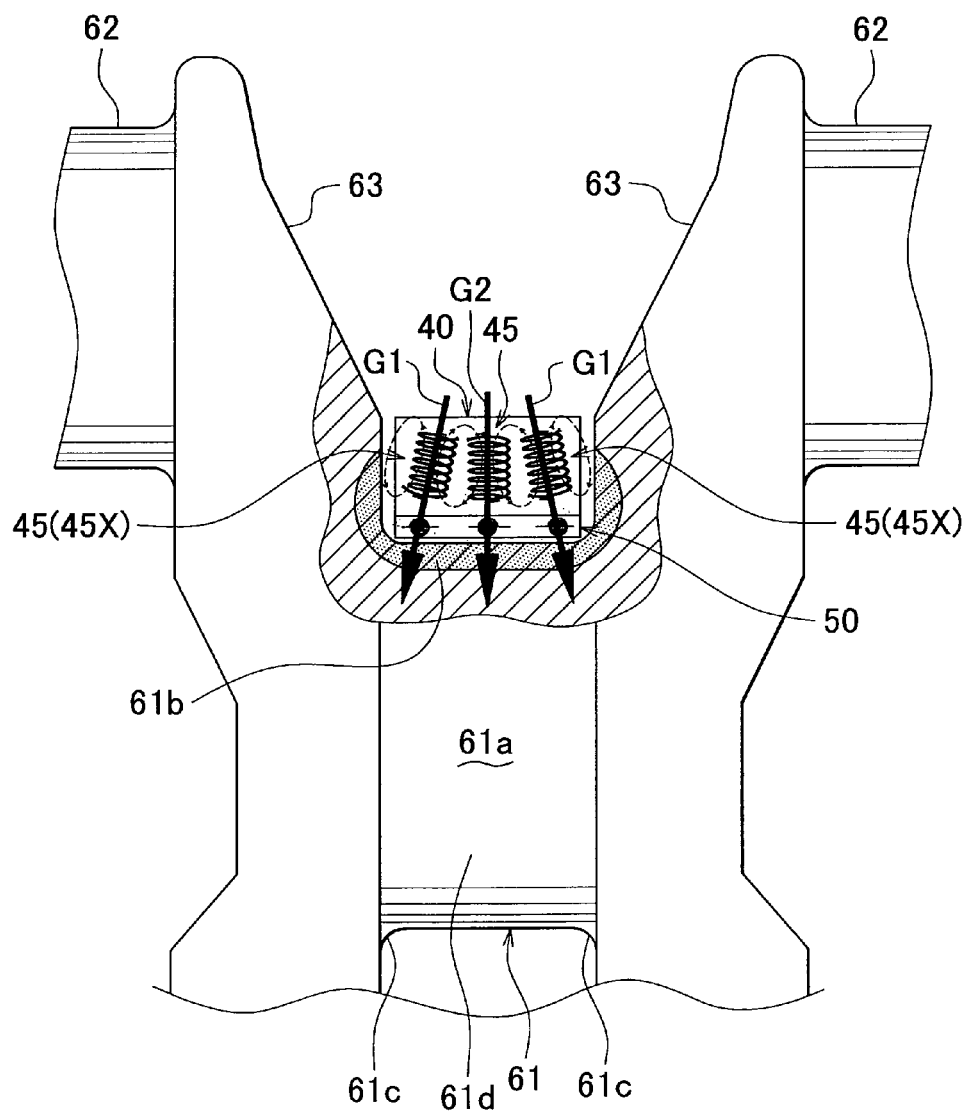
FIG. 19 is a view that shows an application example of the eddy current sensor according to the second embodiment of the invention.

Specifically, as shown in FIG. 19, the crankshaft of a vehicle engine, or the like, generally has journal portions 61 and pin portions 62. The journal portions 61 are shaft portions that are rotated while being supported by main bearings of the crankshaft. The pin portions 62 are portions coupled to the journal portions 61 via arm portions 63, and are shaft portions parallel to the journal portions 61. In addition, in the crankshaft, the journal portions 61 and the pin portions 62 are alternately coupled in the axial direction of the crankshaft (in the horizontal direction in FIG. 19) via the arm portions 63.

In this way, the journal portions 61 and pin portions 62 that are present between the arm portions 63 in the crankshaft are portions that cannot be inserted through an eddy current sensor having a hole (through hole) with a size that allows eddy current measurement in correspondence with the outer diameters of the journal portions 61 or pin portions 62. Then, in order to set a portion, such as the journal portion 61 and the pin portion, that cannot be inserted through the eddy current sensor as a measurement target in eddy current measurement, the eddy current sensor according to the present embodiment formed in a substantially circular arc shape is used.

Figure 18:
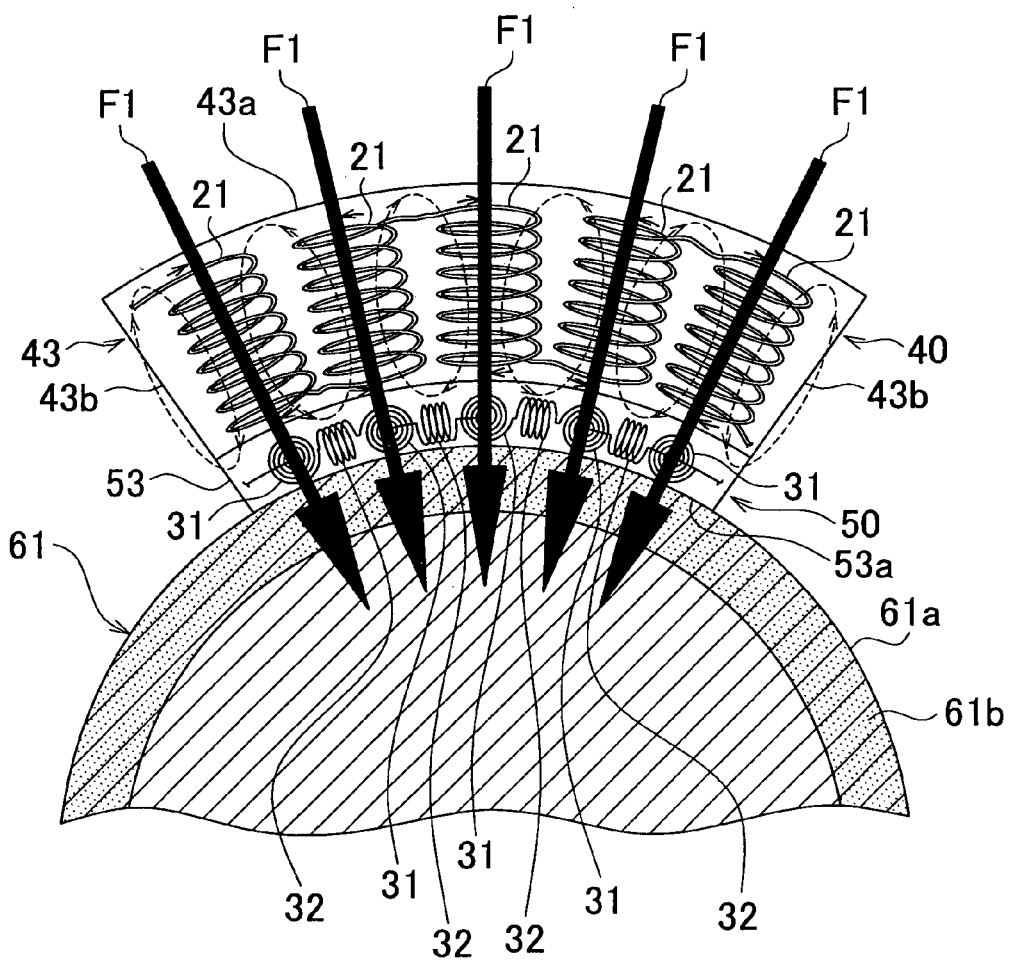
FIG. 18 is a view that shows an application example of the eddy current sensor according to the second embodiment of the invention.

As shown in FIG. 18, each journal portion 61, which is the shaft portion, has a circular outer peripheral surface 61*a*. When the crankshaft is a quenched component, a quench-hardened layer 61*b* is formed in the outer peripheral portion of each journal portion 61. In this way, the journal portion 61 having the quench-hardened layer 61*b* is subjected to eddy current measurement for inspecting quenching quality using the eddy current sensor according to the present embodiment.

That is, as shown in FIG. 18, at the time of eddy current measurement on the journal portion 61, the substantially circular arc-shaped eddy current sensor according to the present embodiment is brought close to the journal portion 61 from the detection coil 50 side and is then set. Here, the eddy current sensor according to the present embodiment is set so that the inner peripheral surface 53a of the second housing 53 of the detection coil 50 is aligned along the outer peripheral surface 61a of the journal portion 61. Then, the eddy current sensor set to the journal portion 61 is appropriately moved in the circumferential direction along the outer peripheral surface 61a of the journal portion 61. By so doing, eddy current measurement is conducted over the entire circumference of the journal portion 61.

With the substantially circular arc eddy current sensor according to the present embodiment, magnetic fields (vertical magnetic fields (Hz)) in the coil central axis direction, formed in the five solenoid coils 21 that constitute each coil row 45 of the excitation coil 40, are formed in directions toward the substantially central axis of the journal portion 61 (substantially in the radial direction of the journal portion 61) (see the arrows F1). That is, with the substantially circular arc eddy current sensor, it is possible to substantially uniformly apply the exciting magnetic field, generated by the excitation coil 40, in the circumferential direction of the journal portion 61. By so doing, it is possible to equalize variations in distance between the excitation coil 40 and the journal portion 61. Then, in eddy current measurement conducted using the eddy current sensor according to the present embodiment, variations in output in the circumferential direction of the journal portion 61 are combined.

Thus, in the substantially circular arc eddy current sensor, the size of the substantially circular arc shape, the shape of the inner peripheral surface 53a formed in the second housing 53, and the like, are set on the basis of the diameter of the shaft portion (journal portion 61), which is the measurement target. Note that the length in the circumferential direction (the size of the central angle) of the substantially circular arc shape of the eddy current sensor is appropriately set at the length of the semi-circle (at a central angle of 180°) or below so as to be able to radially moving the eddy current sensor onto the journal portion 61. In addition, eddy current measurement is conducted on the pin portion 62 (see FIG. 19) using the substantially circular arc eddy current sensor as well, as in the case of the journal portion 61.

Figure 21B:
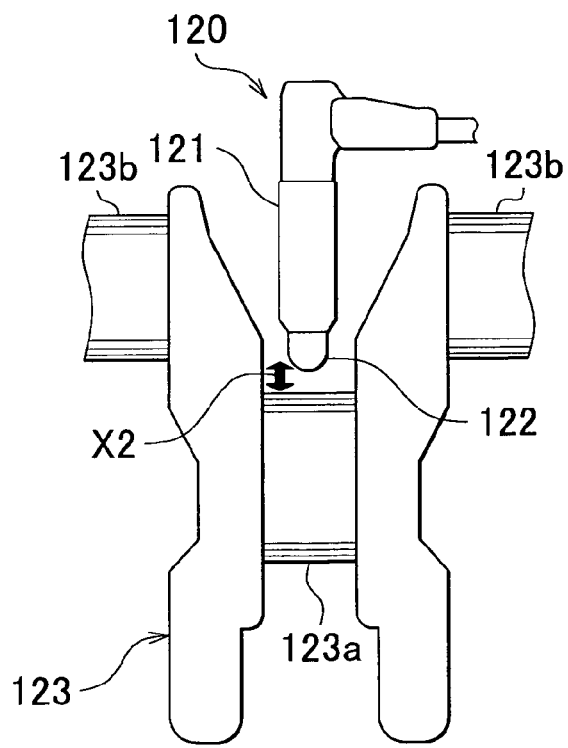
FIG. 21B is a view that shows the configuration of an eddy current sensor according to a related art regarding a probe-type coil.

In this way, with the substantially circular arc eddy current sensor, it is possible to efficiently conduct eddy current measurement with high sensitivity on the journal portion 61 or pin portion 62 of the crankshaft, for which it has been difficult to conduct eddy current measurement using the existing through-type coil (see the through-type coil 110 shown in FIG. 21A) or probe-type sensor (see the probe-type coil 120 shown in FIG. 21B). Note that the eddy current sensor according to the present embodiment may be applied to a non-circular portion, such as a cam portion of a camshaft of an engine, by devising the shape of arrangement of the coils or the shape of the housing.

Figure 17:
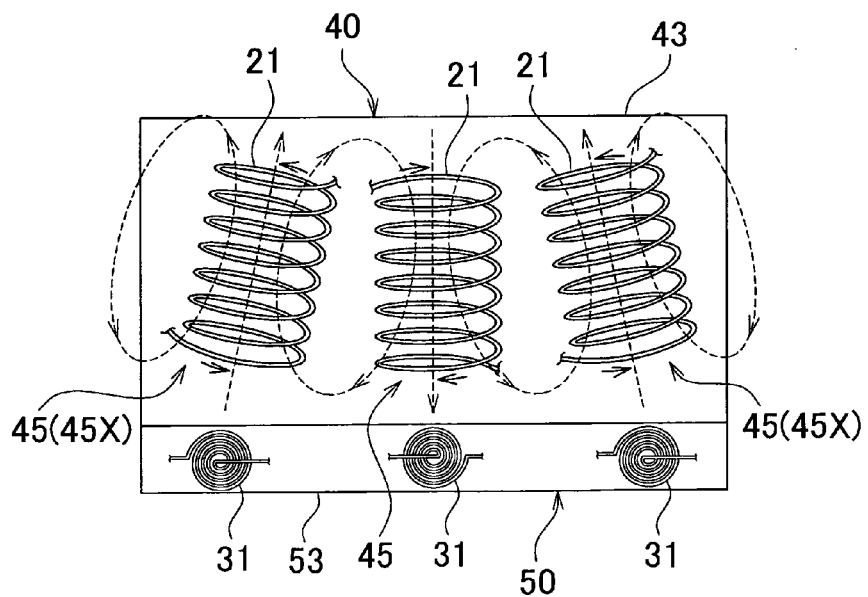
FIG. 17 is a view in the arrow Y direction in FIG. 14.

In addition, in the eddy current sensor according to the present embodiment, each coil row 45 of the excitation coil 40 is arranged at an angle in accordance with the shape of the work piece. That is, as shown in FIG. 17, in the eddy current sensor according to the present embodiment, the excitation coil 40 has inclined coil rows 45X as the coil rows 45. Each inclined coil row 45X is the coil row 45 in which the five solenoid coils 21 are arranged so as to be inclined in accordance with the shape of the work piece in correspondence with the solenoid coils 21 that constitute the other coil rows 45.

As shown in FIG. 17, in the present embodiment, among the three coil rows 45 of the excitation coil 40, the second coil row 45B (see FIG. 14) that is a reference coil row located in the middle in the parallel direction is used as a reference, and the coil rows 45 located on both sides of the second coil row 4513 in the parallel direction (the first coil row 45A and the third coil row 45C (see FIG. 14)) are used as the inclined coil rows 45X.

That is, the solenoid coils 21 that constitute the reference second coil row 45B in the present embodiment are arranged so that the coil central axes are directed to a center position of a predetermined circular shape that sets the series direction as the direction in which the circular arc of the above described substantially circular arc shape is formed. In contrast, the solenoid coils 21 that constitute the first coil row 45A and the third coil row 45C, which are the inclined coil rows 45X, are formed so that the coil central axes are inclined with respect to the coil central axes of the solenoid coils 21 that constitute the second coil row 45B.

Then, in the present embodiment, the inclined coil rows 45X of the excitation coil 40 are inclined so that the ends adjacent to the detection coil 50 are the outer side in the parallel direction. That is, as shown in FIG. 17, the inclined coil rows 45X located on both sides of the second coil row 45B (see FIG. 14) are arranged in an inclined state so that the ends adjacent to the detection coil 50 are spaced away from each other.

Figure 20:
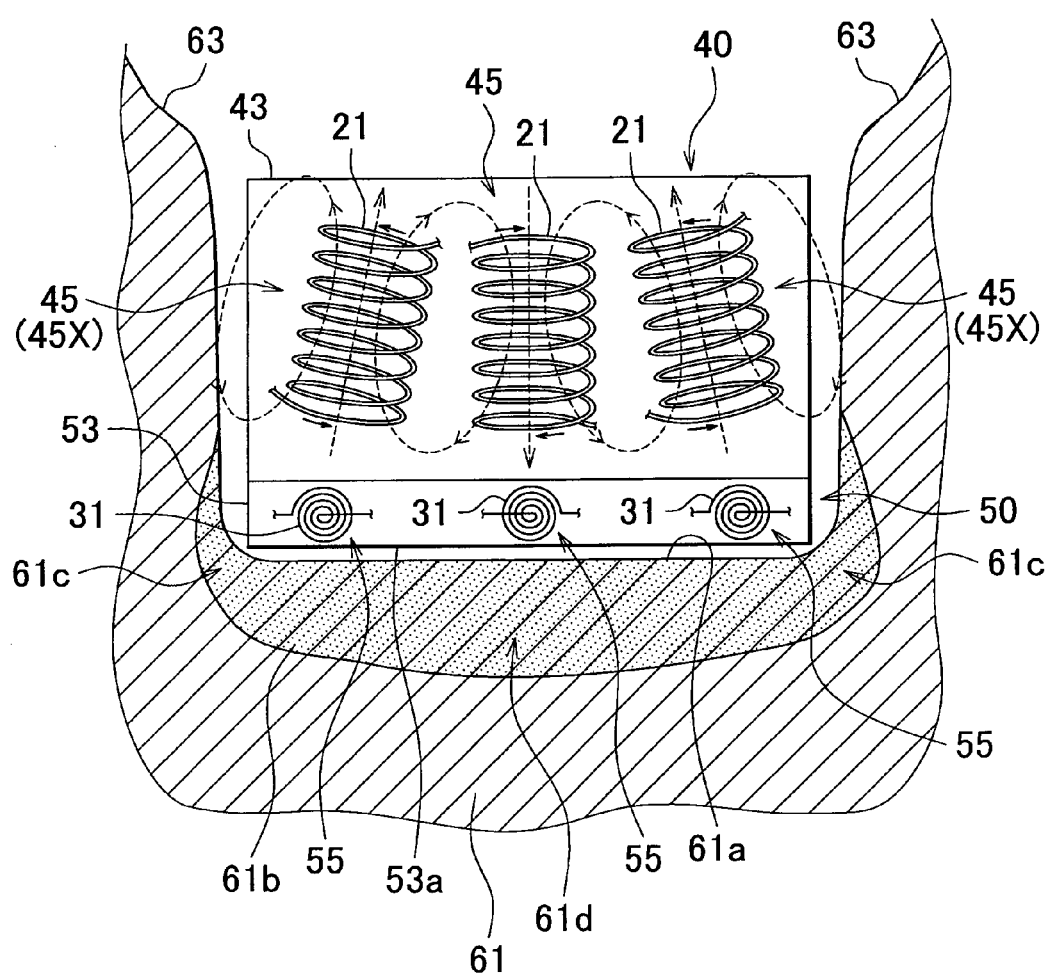
FIG. 20 is an enlarged view of a relevant portion in FIG. 19.

In this way, the eddy current sensor that has the inclined coil rows 45X in the excitation coil 40 is used as follows in eddy current measurement on the journal portion 61 of the crankshaft. That is, as shown in FIG. 19 and FIG. 20, with the eddy current sensor according to the present embodiment, the inclined coil rows 45X are used for measurement on the coupled portion between the journal portion 61 and the arm portion 63, that is, a curved portion 61c that is a portion of the journal portion 61 connected to the arm portion 63. Then, the coil row 45 located in the middle (second coil row 45B) is used for measurement on a shaft middle portion 61d of the journal portion 61.

Thus, the excitation coil 40 is configured so that, in a state where the eddy current sensor according to the present embodiment is set on the journal portion 61 (see FIG. 19 and FIG. 20), the coil central axes of the solenoid coils 21 that constitute the inclined coil rows 45X are directed toward the curved portion 61c. That is, magnetic fields (vertical magnetic fields (Hz)) that are formed in the coil central axis directions in the five solenoid coils 21 that constitute each inclined coil row 45X are formed in directions toward the curved portion 61c (see the arrows G1 in FIG. 19). In addition, magnetic fields (vertical magnetic fields (Hz)) that are formed in the five solenoid coils 21 that constitute the coil row 45 located in the middle (second coil row 45B) and are aligned in the coil central axis directions are formed in directions toward the shaft middle portion 61d (see the arrow G2 in FIG. 19).

In this way, different excitation frequencies are set for the coil rows 45 used for measurement on the curved portion 61c and the shaft middle portion 61d in accordance with the respective portions. Specifically, as shown in FIG. 20, the quench-hardened layer 61b formed in the journal portion 61 extends to the curved portion 61c. Then, the quench depth of the quench-hardened layer 61b is shallower at the curved portion 61c than at the shaft middle portion 61d. Then, a relatively high excitation frequency is set for the inclined coil row 45X used for measurement on the curved portion 61c of which the quench depth is relatively shallow, and a relatively low excitation frequency is set for the coil row 45 used for measurement on the shaft middle portion 61*d* of which the quench depth is relatively deep.

As for an example of setting of the excitation frequency, the excitation frequency is set at a high frequency of 500 Hz for the solenoid coils 21 that constitute each inclined coil row 45X used for measurement on the curved portion 61*c*. In addition, the excitation frequency is set at a low frequency of 50 Hz for the solenoid coils 21 that constitute the coil row 45 used for measurement on the shaft middle portion 61*d*.

In addition, the frequencies of amplified phase detection signals in the three coil groups 55 of the detection coil 50 are also set in correspondence with the excitation frequencies of the corresponding coil rows 45. That is, the frequency of an amplified phase detection signal is set at a high frequency of 500 Hz for the coils that constitute the coil groups 55 (the first coil group 55A and the third coil group 55C) corresponding to the inclined coil rows 45X. The frequency of an amplified phase detection signal is set at a low frequency of 50 Hz for the coils that constitute the coil group 55 (second coil group 55B) located in the middle of the three coil rows 45. Note that eddy current measurement conducted using the eddy current sensor having the above inclined coil rows 45X may also be applied to the pin portion 62 (see FIG. 19) as in the case of the journal portion 61.

In this way, with the eddy current sensor having the inclined coil rows 45X, it is possible to conduct measurement on both curved portions 61*c* and shaft middle portion 61*d* in the axial direction of the journal portion 61 at the same time. Then, it is possible to conduct accurate eddy current measurement according to the quench depth as an inspection for quenching quality on a portion having a shape, such as the journal portion 61 or pin portion 61 of the crankshaft.

Note that, in the eddy current sensor according to the present embodiment, the number and arrangement shape of the solenoid coils 21 that constitute each coil row 45 of the excitation coil 40 and the number and arrangement shape of the coils (pancake coils 31 and the horizontal solenoid coils 32) that constitute each coil group 55 of the detection coil 50 are not specifically limited. Furthermore, each of the plurality of solenoid coils 21 of the excitation coil 40 may be configured to be able to apply an alternating-current excitation signal independently. Similarly, each of the plurality of coils of the detection coil 50 may also be configured to be able to detect a detection signal independently.

With the eddy current sensor described in the above embodiments, it is possible to conduct 100 percent inspection (100 percent assurance) by means of in-line inspection on the quenching quality. By so doing, it is possible to omit a torsion test through sampling, which is destructive test conducted in the existing art, and it is possible to reduce cost and work time with the omission of torsion test. As a result, the quenching quality may be improved, and cost and time may be reduced in inspection of the quenching quality.

In addition, when inspection of the quenching quality is successively conducted on a plurality of work pieces, an eddy current measurement result is constantly monitored. By so doing, for example, when there is a quenching problem, such as a clogging of coolant and steep fluctuations in power, in a system for applying quenching, such as induction quenching, the problem may be detected in real time, and early measures may be taken for the quenching problem.

In addition, eddy current measurement values of all components are acquired in an actual assembly line, or the like, to thereby make it possible to traceability management. In conjunction with this, it is possible to find a correlation between occurrence of the above quenching problem and occurrence of a quenching failure in a work piece, so it is possible to obtain manufacturing requirements and management requirements for a non-defective product.

In the above described embodiments of the invention, the case where eddy current measurement is used for inspecting the quenching quality is mainly illustrated; however, the eddy current sensor according to the aspect of the invention may be applied to another inspection for inspecting a measurement target component through eddy current measurement, such as an inspection of a surface texture other than the quenching quality, an inspection of defects such as cracks, and discrimination of foreign materials.

The invention claimed is:

1. An eddy current sensor comprising:
an excitation coil for applying a predetermined alternating-current excitation signal to a measurement target component, wherein the excitation coil has a plurality of solenoid coils; and
a detection coil for detecting a detection signal, generated by eddy current, from the measurement target component to which the alternating-current excitation signal is applied, wherein the detection coil is arranged on at least one of two sides of the excitation coil in a direction of a central axis of each solenoid coil, wherein
the detection coil includes at least a first coil that is sensitive to a magnetic field in the central axis direction of each solenoid coil and a second coil that is sensitive to a magnetic field formed between the adjacent solenoid coils in a direction substantially perpendicular to the central axis of each solenoid coil, wherein
the plurality of solenoid coils are arranged side by side with one another so that winding directions of the adjacent solenoid coils are opposite to each other by winding a single continuous lead wire so that upper or lower ends of the adjacent solenoid coils are alternately coupled to each other in order to generate a revolving magnetic field by the interaction between the adjacent solenoid coils.

2. The eddy current sensor according to claim 1, wherein the plurality of solenoid coils are arranged side by side so that the central axes are parallel to one another.

3. The eddy current sensor according to claim 2, wherein the plurality of solenoid coils are arranged annularly so as to form a ring.

4. The eddy current sensor according to claim 2, wherein the excitation coil has a plurality of coil rows, each of which is able to apply the alternating-current excitation signal independently, the plurality of solenoid coils in each coil row are arranged in a predetermined direction, and the plurality of coil rows are arranged in a state where winding directions of the adjacent solenoid coils are opposite to each other.

5. The eddy current sensor according to claim 1, wherein the plurality of solenoid coils are arranged side by side in a state where the coil central axes are inclined with respect to a vertical direction.

6. The eddy current sensor according to claim 5, wherein the plurality of solenoid coils are arranged annularly so as to form a ring.

7. The eddy current sensor according to claim 6, wherein the plurality of solenoid coils are arranged at an angle with respect to the central axis of the ring formed of the plurality of solenoid coils arranged annularly, so that ends on the same side on the coil central axis direction are directed inwardly of the ring.

8. The eddy current sensor according to claim 5, wherein the excitation coil has a plurality of coil rows, each of which is able to apply the alternating-current excitation signal independently, the plurality of solenoid coils in each coil row are arranged in a predetermined direction, and the plurality of coil rows are arranged in a state where winding directions of the adjacent solenoid coils are opposite to each other.

9. The eddy current sensor according to claim 8, wherein arrangement of the plurality of solenoid coils in each coil row is curved with respect to the predetermined direction to form a substantially circular are shape so that the coil central axis of the solenoid coils that constitute each coil row of the excitation coil are arranged so as to be directed toward the center of the circular arc.

10. The eddy current sensor according to claim 8, wherein the plurality of coil rows include a reference coil row and a coil row with inclined central axis that is arranged so as to be inclined with respect to the central axis of the reference coil row so that the ends adjacent to the detection coil are spaced away from each other.

11. The eddy current sensor according to claim 1, further comprising:
   a first housing that supports the plurality of solenoid coils of the excitation coil; and
   a second housing that supports the detection coil, wherein the second housing is detachable with respect to the first housing.

12. The eddy current sensor according to claim 11, wherein the second housing is stacked on the first housing.

13. An inspection method using an eddy current sensor, comprising:
   inspecting a measurement target component by conducting eddy current measurement using the eddy current sensor according to claim 1.

\* \* \* \* \*